US010059957B2

(12) United States Patent
He et al.

(10) Patent No.: US 10,059,957 B2
(45) Date of Patent: *Aug. 28, 2018

(54) PLANT HEAT-RESISTANCE GENE JAZ5A AND USE THEREOF

(71) Applicant: Shanghai Institutes for Biological Sciences, Chinese Academy of Sciences, Shanghai (CN)

(72) Inventors: Yu-Ke He, Shanghai (CN); Chuan-Bao Sun, Shanghai (CN)

(73) Assignee: SHANGHAI INSTITUTES FOR BIOLOGICAL SCIENCES, CHINESE ACADEMY OF SCIENCES, Shanghai (CN)

(*) Notice: Subject to any disclaimer, the term of this patent is extended or adjusted under 35 U.S.C. 154(b) by 0 days.

This patent is subject to a terminal disclaimer.

(21) Appl. No.: 15/014,682

(22) Filed: Feb. 3, 2016

(65) Prior Publication Data

US 2016/0152996 A1 Jun. 2, 2016

Related U.S. Application Data

(62) Division of application No. 13/808,627, filed as application No. PCT/NL2011/050499 on Jul. 7, 2011, now Pat. No. 9,284,572.

(30) Foreign Application Priority Data

Jul. 8, 2010 (CN) .......................... 2010 1 0222842

(51) Int. Cl.
*C12N 15/82* (2006.01)
*C07K 14/415* (2006.01)

(52) U.S. Cl.
CPC ........ *C12N 15/8273* (2013.01); *C07K 14/415* (2013.01); *C12N 15/8271* (2013.01)

(58) Field of Classification Search
CPC ................................................ C12N 15/8273
See application file for complete search history.

(56) References Cited

U.S. PATENT DOCUMENTS

| 6,515,202 | B1 | 2/2003 | Crane et al. |
| 7,482,510 | B2 | 1/2009 | da Costa e Silva et al. |
| 2006/0107345 | A1* | 5/2006 | Alexandrov ......... C07K 14/415 800/278 |
| 2009/0158466 | A1 | 6/2009 | Wan et al. |
| 2010/0037352 | A1 | 2/2010 | Alexandrov et al. |
| 2013/0167266 | A1 | 6/2013 | He et al. |

FOREIGN PATENT DOCUMENTS

| CN | 101585870 | 11/2009 |
| CN | 101585871 | 11/2009 |
| CN | 101638658 | 2/2010 |
| EP | 1 586 645 A2 | 10/2005 |
| WO | WO-99/04013 A2 | 1/1999 |
| WO | WO-2004/020642 | 3/2004 |
| WO | WO-2006/055631 A2 | 5/2006 |
| WO | WO-2012/005591 | 1/2012 |

OTHER PUBLICATIONS

Friedberg (Brief. Bioinformatics (2006) 7: 225-242).*
Altschul, et al. "Basic Local Alignment Search Tool", J. Mol. Biol, 1990, vol. 215, pp. 403-410.
Chini et al., "The JAZ family of repressors is the missing link jasmonate signalling" Nature, Aug. 9, 2007, vol. 448, pp. 666-671.
Database Geneseq [Online] Mar. 1, 2012, "*Brassica rapa* subsp. *chinensis* BccJAZ5a protein sequence, SEQ:2", Database Assession No. XP 002684038.
Database Geneseq [Online] Mar. 1, 2012, "*Brassica rapa* subsp. *chinensis* BccJAZ5a protein sequence, SEQ:4", Database Assession No. XP 002684037.
Database Geneseq [Online] Sep. 30, 2010, "Plant isolated polypeptide sequence, SEQ ID 825,", Database Assession No. XP 002684035.
Devereux, et al. "A Comprehensive set of sequence analysis programs for the VAX", Nucleic Acids Research, 1984, vol. 12, No. 1, pp. 387-395.
Gelvin, Agrobacterium-Mediated plant transformation: the biology behind the "Gene-Jockeying" Tool, Microbiology and Molecular Biology Reviews, Mar. 2003, vol. 67, No. 1, pp. 16-37.
Search Report received in International Application No. PCT/NL2012/050481 dated Oct. 9, 2012.
Seo, Yean Joo et al., "Overexpression of the Ethylene-Responsive Factor Gene CrERF4 from *Brassica rapa* Increases Tolerance to Salt and Drought in *Arabidopsis* Plants,", Molecules and Cells, vol. 30, No. 3, Sep. 2010, pp. 271-277.
Database Genebank [Online], Sep. 16, 2008, XP000002657468, Database accession No. AC172887.
Friedberg, "Automated protein function prediction—the genomic challenge", 7 Briefings in Bioinformatics No. 3, 225-242 (2006).
Guo et al., "Protein tolerance to random amino acid change", PNAS, Jun. 22, 2004, vol. 101, No. 25, pp. 9205-9210.
International Search Report received in the parent application PCT/NL2011/050499, dated Sep. 19, 2011.
Kaur, et al., "Genetic map construction and QTl mapping of resistance to blackleg (*Leptosphaeria maculans*) disease in Australian canola (*Brassica napus* L.) cultivars", Theoretical and Applied Genetics, vol. 120, No. 1, 2009, pp. 71-83.
Lacombe, et al. Science (2001), vol. 292, pp. 1486-1487.
Sequence Alignment of SEQ ID No. 2—Generated on Jul. 30, 2015.
Wang, et al. "Plant responses to drought, salinity and extreme temperatures: towards genetic engineering for stress tolerance", Planta, 2003, vol. 218, pp. 1-14.

(Continued)

*Primary Examiner* — Lee A Visone
(74) *Attorney, Agent, or Firm* — Foley & Lardner LLP; Sunit Talapatra; Tianran Yan

(57) ABSTRACT

The present invention provides a heat-resistance plant gene JAZ5a and use thereof. The inventors of the present invention isolated for the first time a heat resistance gene from the plant of *Brassica* spp., which can greatly improve the heat-resistance ability of the plant, especially in the bolting stage. The present invention further provides a protein encoded by said gene and its preparation method, vectors and host cells containing said gene, and a method for preparing a transgenic plant containing said gene.

15 Claims, 5 Drawing Sheets

Specification includes a Sequence Listing.

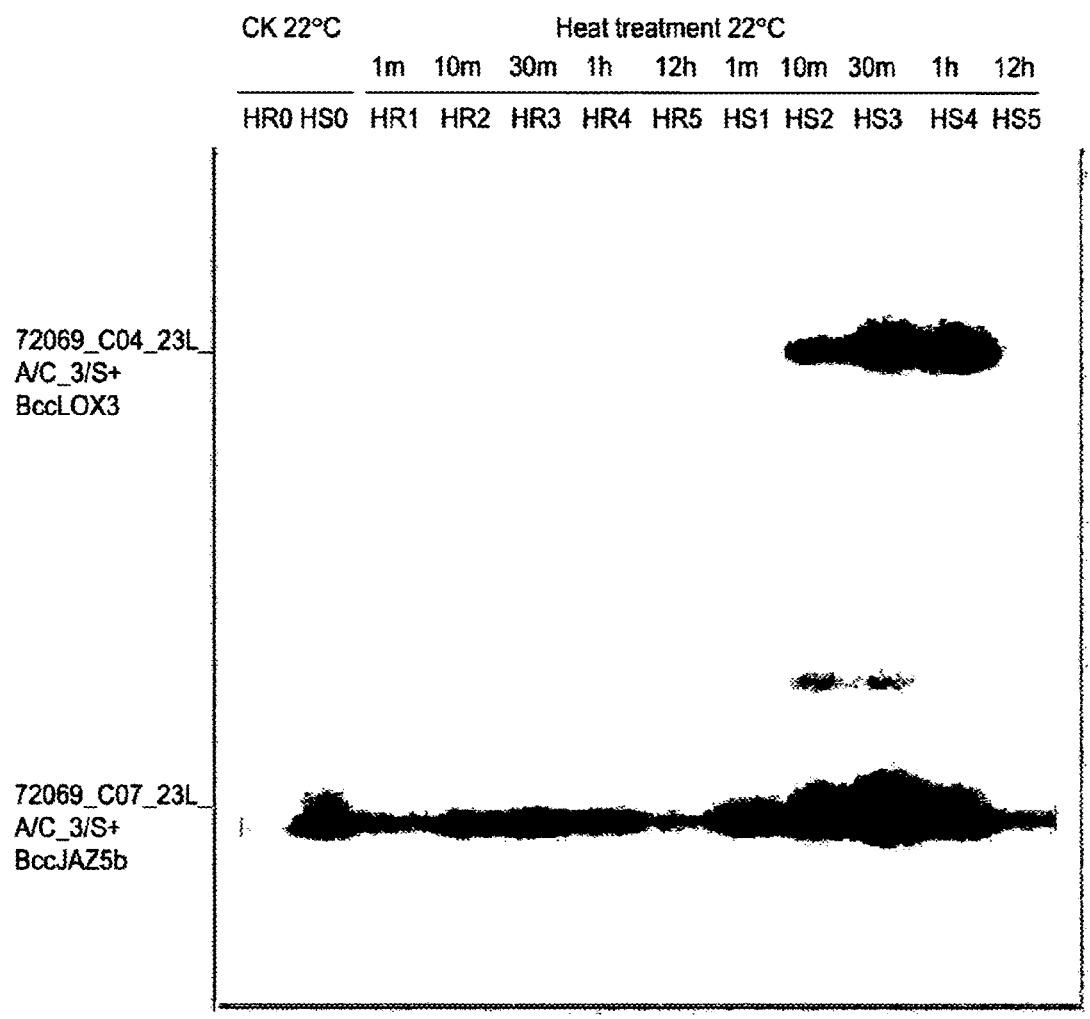

Fig.1 (cont'd)
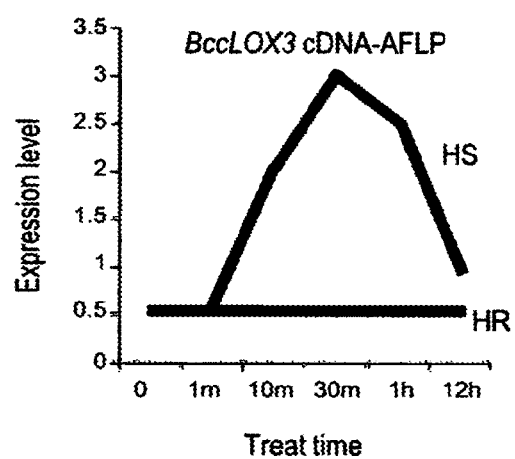
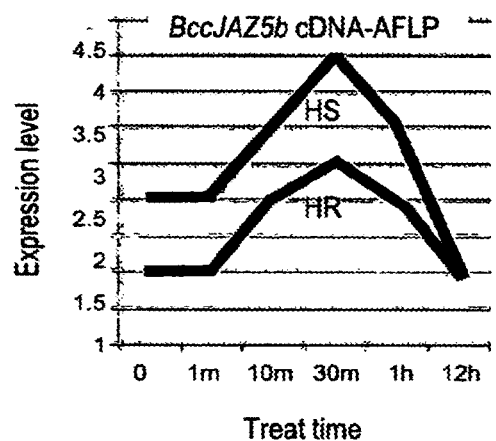

45°C 3 hours     46°C 2.5 hours

PLANT HEAT-RESISTANCE GENE JAZ5A AND USE THEREOF

CROSS-REFERENCE TO RELATED APPLICATIONS

This application is a Divisional of U.S. patent application Ser. No. 13/808,627 filed Mar. 7, 2013, which is the U.S. National Stage of International Patent Application No. PCT/NL2011/050499, filed Jul. 7, 2011, which claims the benefit of Chinese Patent Application No.: 201010222842.3, filed Jul. 8, 2010, all of which are incorporated herein by reference in their entirety.

The instant application contains a Sequence Listing which has been submitted in ASCII format via EFS-WEB and is hereby incorporated by reference in its entirety. Said ASCII copy, created on Feb. 3, 2016, is named Sequence.txt and is 10.5 KB.

TECHNICAL FIELD

The present invention belongs to the fields of biotechnology and botany. The present invention relates to a new method for improving heat resistance of a plant. The invention involves the use of a protein in said plant for improving heat resistance. The present invention relates to the enhancement of the expression or activity of the protein, thereby providing improved heat resistance to a plant in comparison to a plant not modified to enhance expression of the protein.

BACKGROUND ART

Cabbages mainly include *Brassica campestris* L. ssp. *Pekinensis* and *Brassica campestris* L. ssp. *chinensis*. *Brassica campestris* L. ssp. *chinensis* is also named as green cabbage, and baby *Brassica campestris* L. ssp. *chinensis* in the north of China. *Brassica campestris* L. ssp. *chinensis* exhibits high adaptability, growth, productivity and nutrition. It is the most consumed vegetable among various vegetables and widely grown in the provinces in the regions of Changjiang valley in China. There are various types and varieties of *Brassica campestris* L. ssp. *chinensis*. Cabbages have a short growth period, wide adaptability, and high productivity. They are also easy to plant, which allows for a sustained perennial supply. The products of *Brassica campestris* L. ssp. *chinensis* are fresh and tender, have rich nutrition and win favor of consumers. *Brassica campestris* L. ssp. *chinensis* comprises about 30-40% of the total domestic vegetable productivity a year, and also makes a significant contribution in supplementing vegetables in slack seasons and balancing the vegetable supply over a whole year. Both the *Brassica campestris* L. ssp. *Pekinensis* and *Brassica campestris* L. ssp. *chinensis* favor cool whether and can be planted perennially. The most suitable growth temperature is 15-20° C. In recent years, to meet the market demand, cabbages are mainly planted by the technique of intensive culture. To ensure an even production and supply among the four seasons, *Brassica campestris* L. ssp. *chinensis* generally needs to be planted in different manners in different seasons. In the past, *Brassica campestris* L. ssp. *chinensis* was mainly planted in spring and winter. Now people begin to plant *Brassica campestris* L. ssp. *chinensis* in torrid summer and autumn by various culture manners. This will undoubtedly make *Brassica campestris* L. ssp. *chinensis* subject to the stress from high temperatures during its growth, especially in late spring, summer and early autumn. The *Brassica campestris* L. ssp. *chinensis* cultured in the seasons of high temperature can go to the market in bulk after a 20-day culture. However, the high temperatures usually lead to an elongated internode, slowed growth, bitter taste and undesirably increased fiber, etc. This will result in low productivity and poor quality. As a result, the price rises and the supply falls short of demand. The consumer demand cannot be met. *Brassica campestris* L. ssp. *Pekinensis* has poor tolerance to high temperature. It is highly temperature sensitive in the rosette stage and the heading stage. If the average temperature is too high, the heart leaf can not amplexate to built a tight bulb, or can not bulb up at all. Even if it constrainedly bulbs up, the heading is loose. In the natural field conditions in summer, the production relies on the heat-resistance plants' capability of forming a normal leafy head. And the capability of heading formation under the natural high temperature in fields becomes an indication of a heat-resistance in *Brassica campestris* L. ssp. *Pekinensis*. Both the *Brassica campestris* L. ssp. *Pekinensis* and the *Brassica campestris* L. ssp. *chinensis* were originally planted in China. In foreign countries, there is few studies on breeding of cabbages. Varieties of Japanese, Korean and Formosan origins are poor in heat resistance, and unsuitable for planting in China. Domestically dominant are mainly the disease resistant varieties planted in autumn. Vegetables of cabbages have a narrow gene library for heat-resistance. Breeding of heat-resistance cabbage variety is limited to the screening among the cabbage materials, whereby only some varieties with poor heat resistance and low stress resistance have been obtained. To solve these problems, the domestic breeding experts have utilized the traditional breeding methods to widely screen and culture heat-resistance varieties of vegetables of cabbages, to introduce heat-resistance genes, and broaden the sources of exploitation, which improved the heat-resistance of vegetables of cabbages to a certain degree and have produced effect in actual production. However, the current methods are limited to the assessment of heat resistance under the local climate and the morphological changes under a high temperature stress. These methods are not suitable for the temperate areas, which can not provide the field conditions with suitable selection stresses. Even if a single heat-resistance plant was selected, a series of complicated methods and means would be required to maintain the heat-resistance in the seeds collected until the next spring. The screening requires a long period, and is geographically limited, which can not provide a heat resistant variety universally adaptable. Therefore, it is an urgent task in breeding of heat-resistance vegetables of cabbages to intensively study the occurrence and development of the heat damages during the seedling stage, and to develop a method and technique for screening heat resistance in seedling stage, which provides improved operability, stability, efficiency and adaptability. The traits closely associated with the heat resistance in cabbages are of a quantitative nature, which poses great difficulties in genotyping. Particularly for molecular breeding, the difficulties include not only the limited number of DNA markers useful in the auxiliary selection, but also the inconsistence of the number and the significance of the quantitative traits loci (QTL). Therefore, since the genome sequencing of cabbages is not finished yet, and the study on functional genome study is gaining increasing interests, there is a need for a quick, sensitive and efficient qualitative analysis on the various traits in plant and the DNA profiles, and a quantitative analysis on the phenotypes in plant and changes in gene expressions, which is usefully in the breeding of heat-resistance cabbages. Recently, molecular biology is developing rapidly. Particularly, gene chips have been widely used in molecular breeding of crops. Gene chip technique is one of the greatest achievements having profound influence since the middle of 1990s. It is a new and highly crossing technology which merges microelectronics, biology, physics, chemistry and computer science. Gene chip comprises a support on which a lot of specific oligonucleotide fragments or gene fragments as probes are arranged and fixed, which forms a DNA microarray. The DNA or RNA in a sample is fluorescently labeled via various techniques such as PCR amplification and in vitro transcription. After the probes hybridize to the labeled molecules in the sample, the chip is scanned by a fluorescence detection system and the fluorescent signals of all the probes are compared and measured by using a computer system. By obtaining the strength of detected hybridization signal of each probe molecule, the information concerning the amount and sequence of the sample molecule could be quickly obtained. Currently, gene chip technique has been widely used in various fields, such as drug screening, agriculture, diagnosis and treatment of disease, identification of species of traditional Chinese medicine, judicial expertise, supervise on food and sanitation, environment detection, national defense and the like. There are not many reports about using gene chips in plants. The reports mainly focus on *Arabidopsis thaliana*, strawberry, and morning glory and the like. With respect to the applications of gene chips, analysis and detection of gene expression level may be the most popular and established. Since thousands of probes can be fixed onto a chip, it is possible to simultaneously detect a lot of genes. This not only allows for comparing different transcription levels under different conditions for a lot of genes in one genome, but also comparing different transcription levels of corresponding genes in different genomes. Thus, it overcomes the bottlenecks in the previous studies, wherein only one or two of genes could be studied at a time. Therefore, there is a need for a method of developing a plant heat-resistance gene by utilizing the chip technique, so as to obtain some valuable plant heat-resistance genes.

SUMMARY OF THE INVENTION

It is an objective of the current invention to provide for heat resistance in a plant. With plants provided with heat resistance it is e.g. possible to obtain higher yields of crop and/or plant product when the plant is subjected to a period or periods of heat when compared to plants not provided with heat resistance. It was found a plant can be provided with heat resistance when the expression in said plant of a JAZ5a gene is enhanced. The present invention thus provides for an isolated plant heat-resistance protein and to methods and uses thereof.

In one embodiment, an isolated plant heat-resistance protein is provided, which is:
(a) a protein having the amino acid sequence of SEQ ID NO:4; or
(b) a protein derived from the protein of (a) by substitution, deletion or addition of one or more residues in the amino acid sequence of SEQ ID NO:4 and having an equivalent function as the amino acid sequence represented by SEQ ID NO:4; or
(c) a protein derived from the protein of (a), having at least 60% identity to the amino acid sequence of SEQ ID NO:4 and having an equivalent function as the amino acid sequence represented by SEQ ID NO:4.

In one embodiment, an isolated plant heat resistance protein has at least 60%, 65%, 70%, 75%, 80%, 85%, 90%, 92%, 95%, 96%, 97%, 98% or 99% identity with the amino acid sequence represented by SEQ ID NO: 4. In one embodiment, 1-20, preferably 1-10, more preferable 1-5, most preferably 1-3 residues are substituted, deleted or added in the amino acid sequence of SEQ ID NO: 4.

In one embodiment, the plant is a plant of Cruciferae. In one embodiment, the Cruciferae plant is selected from the group consisting of *Brassica* spp. plant and *Abrabidopsis* spp. plant.

In one embodiment, the *Brassica* spp. plant is *Brassica campestris* ssp. *pekinensis*. In one embodiment, the *Abrabidopsis* spp. plant is *Arabidopsis thaliana* (L.) Heynh.

In one embodiment, the plant heat-resistance protein is derived from the *Brassica* spp. Plan, preferably, it is derived from *Brassica campestris* L. ssp. *chinensis*.

In one embodiment of the present invention, an isolated polynucleotide is provided, which is selected from the group consisting of:
(i) a polynucleotide encoding said protein; or
(ii) a polynucleotide complementary to the polynucleotide of (i).

In one embodiment, the nucleotide sequence of said polynucleotide is SEQ ID NO: 1 or 2.

In one embodiment, a vector is provided, which contains said polynucleotide.

In one embodiment, a genetically engineered host cell is provided, which comprises said vector or said polynucleotide, which may be integrated int the genome of said host cell.

In one embodiment, a plant is provided, which contains any of the aforementioned polynucleotides.

In one embodiment, a method for preparing the aforementioned protein is provided, which comprises:
(a) culturing said host cell under conditions suitable for expression;
(b) isolating said protein from the culture.

In one embodiment, use of the aforementioned protein or its coding gene is provided for improving the heat-resistance of a plant or providing heat resistance to a plant.

In one embodiment, the aforementioned protein or its coding gene is used for improving the heat-resistance of a plant in bolting stage.

In one embodiment, a method for improving the heat-resistance of a plant is provided, which comprises enhancing the expression or activity of the aforementioned protein in said plant.

In one embodiment, said method comprises transforming the polynucleotide encoding the aforementioned protein into the genome of the plant.

In another preferred embodiment, said method comprises:
(1) providing an *agrobacterium* having an expression vector comprising the coding sequence of the aforementioned protein;
(2) providing a plant cell, organ or tissue;
(3) contacting said plant cell, organ or tissue with the *agrobacterium* of step (1), such that the coding sequence of the protein is introduced into the plant cell; (4) optionally, selecting the plant cell, organ or tissue comprising the introduced coding sequence of the protein;
(4) regenerating the plant cell, organ or tissue of step (3) into a plant.

In one embodiment, the introduced coding sequence is integrated into the genome of the plant cell.

In another aspect of the present invention, a transgenic plant obtained or obtainable by the aforementioned method is provided.

In one embodiment of the present invention, a molecular marker for identifying heat-resistance or improved heat-resistance in a plant is provided, wherein said molecular marker comprises at least 50 nucleotides of the sequence of SEQ ID. No 1 or 2. In one embodiment, a method is provided wherein said molecular marker is identified in a plant by sequencing the DNA of a plant cell. In one embodiment, a method is provided wherein said molecular marker is identified by amplifying the said sequence of SEQ ID No. 1 or 2 and detecting the amplicon. In one embodiment, a pair of primers is provided capable of amplifying the said sequence of SEQ ID No. 1 or 2. In one embodiment, a pair of primers is provided represented by the nucleotide sequences SEQ ID NO: 5 and 6.

The other aspects of the present invention will be apparent to the skilled person based on the contents disclosed herein.

BRIEF DESCRIPTION OF THE DRAWINGS

FIG. 1 shows the cDNA-AFLP results of BccLOX3 and BccJAZ5 in the heat-resistant and heat-sensitive varieties of *Brassica chinensis*. The numbers 0, 1, . . . , and 5 in HS0, HS1, . . . , and HS5 indicate the number of treatments, respectively, which correspond to the sampling times indicated above them. "m" means minutes and "h" means hours.

FIG. 3 shows the heat-resistant phenotype of the T2 generation of the transgenic plant 35S::BccJAZ5a.

Panel A shows the expression levels of BccJAZ5a and endogenous AtJAZ5 in the transgenic plant (gBccJAZ5a) and the wild type plant (Col) by RT-PCT. gBccJAZ5A HR/Col T2 indicates the heterozygous plant of the second generation propagated from a transgenic *Arabidopsis* plant transformed with BccJAZ5A genomic DNA ("g" indicates the genomic DNA). In the symbols 1-1, 1-2, 2-1, 2-2, 3-1, 3-2, the numbers before "-" respectively indicate transgenic plants 1, 2 and 3 and the numbers after "-" respectively indicate two repeated experiments of the transgenic plants. Col-1 and Col-2 indicate two experiments for wild type *Arabidopsis*.

Panel B shows transgenic plants and wild type plants subjected to the heat treatment. The 7-day old seedlings were cultivated at 22° C., then subjected to heat treatment at 44-46° C. for 1 hour, and then back to 22° C. for another 7 days before photos were taken.

Panel C shows the growth status of 3 transgenic plants in seedling stage. Under the normal growth conditions, plants of number 2 (#2) transgenic lineage are smaller than plants of the other two transgenic lineages.

Figure 2:
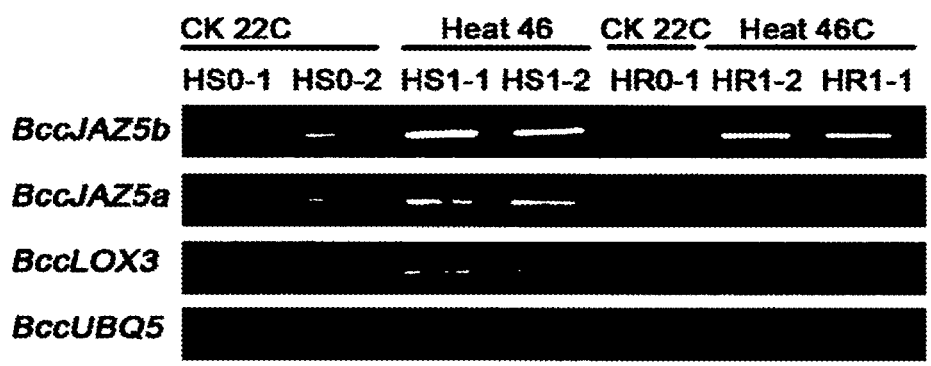
FIG. 2 shows the transcription levels of BccJAZ5a and BccJAZ5b in the heat-resistant and heat-sensitive varieties of *Brassica chinensis* as detected by RT-PCR. After a heat treatment at 46° C. for one hour, total RNA was extracted. UBQ5 is the control. CK indicates the control that was not subjected to a heat treatment, that is, it was subjected to a normal growth temperature. 0-1 and 1-2 indicate two repeated experiments for the controls, and 1-1 and 1-2 indicate two repeated experiments of heat-treatment.
Figure 3:
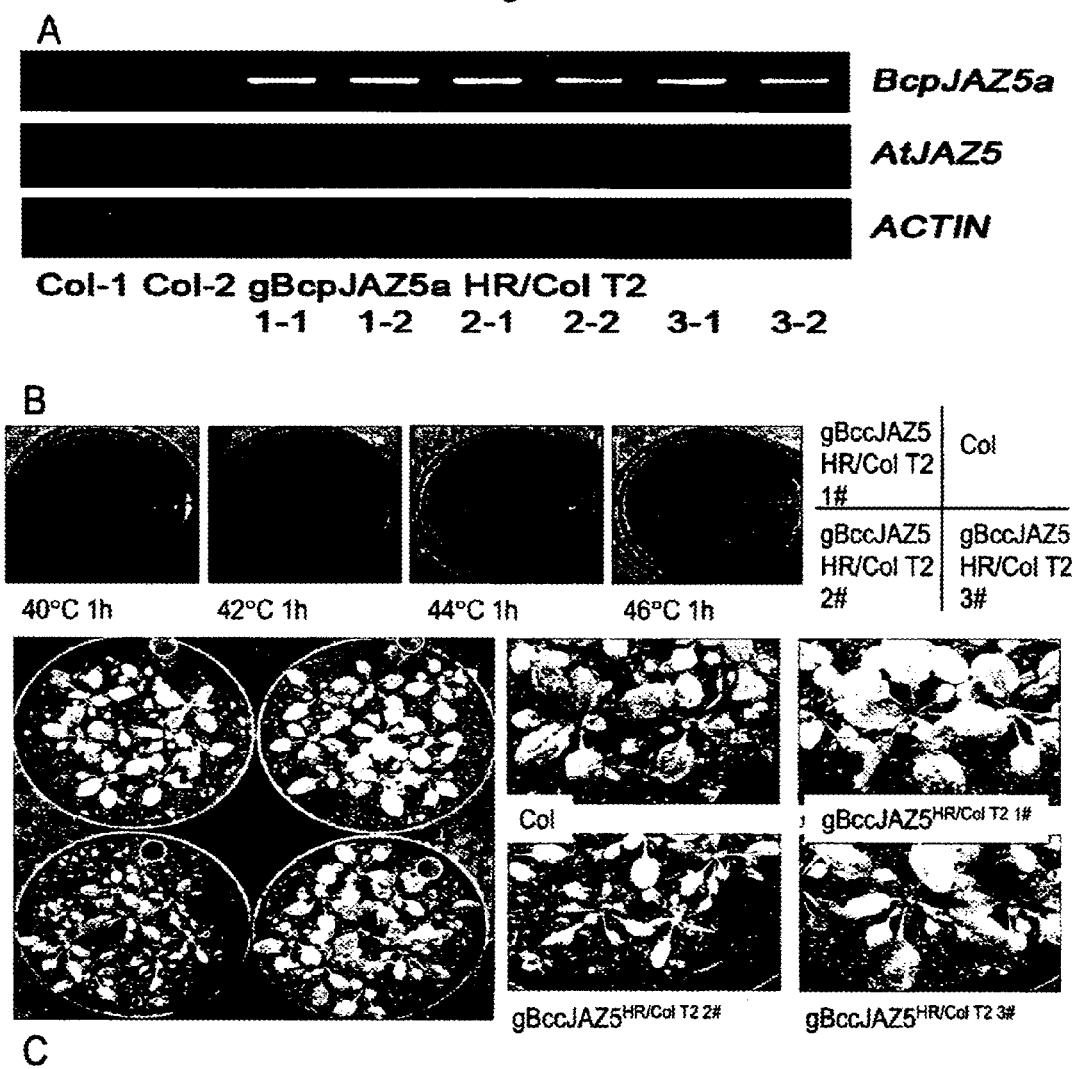
Figure 4:
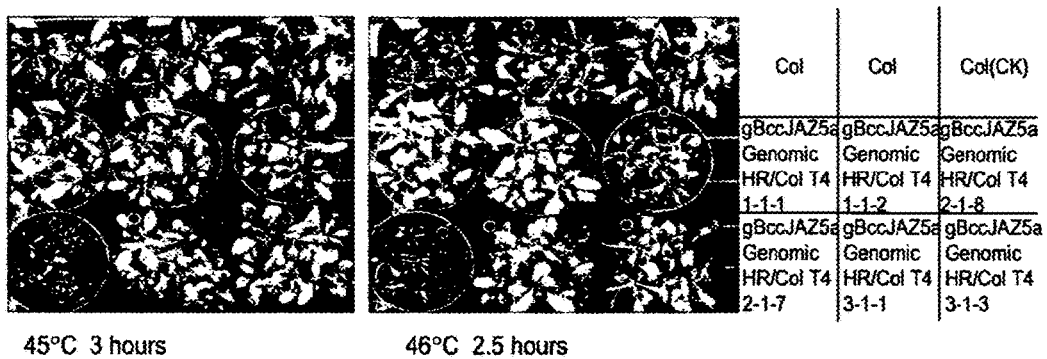

FIG. 4 shows that the 35S::BccJAZ5a transgenic lineages have improved heat-resistance in bolting stage. The plants were cultivated at 22° C. until bolting, and then subjected to heat treatment at 45° C. for 3 hours or at 46° C. for 2.5 hours, transferred to 44° C. for 60 minutes, and then switched back to 22° C. for another 5 days before photos were taken. For each lineage, two experiments in duplicate were conducted. In the figure, the symbols 1-1-1 and 1-1-2 respectively indicate two T2 generation plants of the transgenic lineage 1, symbol 2-1-8 indicates one T2 generation plant of the transgenic lineage 2, and 2-1-7 indicates another T2 generation plant of the transgenic lineage 2. Likely, 3-1-1 and 3-1-3 indicate two T2 generation plants of the transgenic lineage 3.

Figure 5:
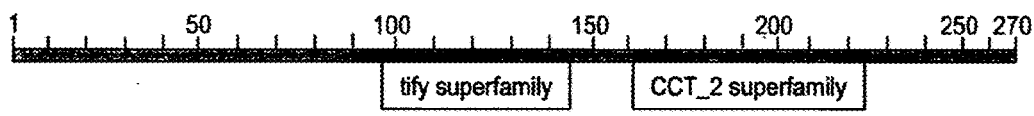

FIG. 5 shows the analysis of the domains in the BccJAZ5a protein (SEQ ID NO:4).

DEFINITIONS

In the following description and examples, a number of terms are used. In order to provide a clear and consistent understanding of the specification and claims, including the scope to be given to such terms, the following definitions are provided. Unless otherwise defined herein, all technical and scientific terms used have the same meaning as commonly understood by one of ordinary skill in the art to which this invention belongs. The disclosures of all publications, patent applications, patents and other references are incorporated herein in their entirety by reference.

Methods of carrying out the conventional techniques used in methods of the invention will be evident to the skilled worker. The practice of conventional techniques in molecular biology, biochemistry, computational chemistry, cell culture, recombinant DNA, bioinformatics, genomics, sequencing and related fields are well-known to those of skill in the art and are discussed, for example, in the following literature references: Sambrook et al., Molecular Cloning. A Laboratory Manual, 2nd Edition, Cold Spring Harbor Laboratory Press, Cold Spring Harbor, N. Y., 1989; Ausubel et al., Current Protocols in Molecular Biology, John Wiley & Sons, New York, 1987 and periodic updates; and the series Methods in Enzymology, Academic Press, San Diego.

In this document and in its claims, the verb "to comprise" and its conjugations is used in its non-limiting sense to mean that items following the word are included, but items not specifically mentioned are not excluded.

As used herein, the singular forms "a," "an" and "the" include plural referents unless the context clearly dictates otherwise. For example, a method for isolating "a" DNA molecule, as used above, includes isolating a plurality of molecules (e.g. 10's, 100's, 1000's, 10's of thousands, 100's of thousands, millions, or more molecules).

As used herein, the term "heat stress" or "heat" refers to a sub-optimal environmental condition associated with temperature. As used herein, the term "heat" refers to an environmental condition wherein the temperature of the atmosphere and/or soil is higher than optimal for growth and/or development. For example, the optimal temperature of the atmosphere for growing cabbages is in the range of 15-20° C. When the temperature is higher than that range, the cabbages are subjected to "heat stress". The effect of subjecting plants to "heat stress" may be that plants do not have optimal growth and/or development. For example, subjecting *Brassica campestris* L. ssp. *chinensis* to heat stress may have the effect of elongating internode, slowing growth, providing bitter taste, increasing fiber content etc. Subjecting *Brassica campestris* L. ssp. *Pekinsis* to heat stress during the rosette stage and the heading stage may have the effect that the heart leaf can not amplexate to built a tight bulb, or it can not bulb up at all. Even if the heart leaf constrainedly bulbs up, the heading may be loose.

The term "heat resistant" or "heat resistance" refers to plants which, when provided with heat resistance (or being heat resistant), when subjected to heat stress do not show effects or show alleviated effects as observed in plants not provided with heat resistance When a plant is "heat resistant", it is capable of sustaining normal growth and/or normal development when being subjected to a high temperature that otherwise would have resulted in reduced growth and/or development normal plants. Hence, heat resistance is a relative term determined by comparing plants with another plant, whereby the plant most capable of sustaining (normal) growth may be a "heat resistant" plant, whereas the plant less capable may be termed a "heat sensitive" plant.

Providing heat resistance thus is understood to include improving the heat resistance of a plant, when compared with a plant not provided with heat resistance.

Aligning and alignment: With the term "aligning" and "alignment" is meant the comparison of two or more nucleotide sequences based on the presence of short or long stretches of identical or similar nucleotides. Several methods for alignment of nucleotide sequences are known in the art, as will be further explained below.

"Expression of a gene" refers to the process wherein a DNA region, which is operably linked to appropriate regulatory regions, particularly a promoter, is transcribed into an RNA, which is biologically active, e.g. which is capable of being translated into a biologically active protein or peptide or active peptide fragment. An active protein in certain embodiments refers to a protein being constitutively active. The coding sequence is preferably in sense-orientation and encodes a desired, biologically active protein or peptide, or an active peptide fragment.

"Functional", in relation to proteins (or variants, such as orthologs or mutants, and fragments), refers to the capability of a gene and/or encoded protein to have an effect on a quantitative and/or qualitative feature(s) of a plant. By modifying the expression level of the gene (e.g. by enhancing expression or reducing expression) the quantitative and/or qualitative feature of a plant is affected. For example, when a protein has a function in heat resistance, enhancing gene expression may lead to heat resistance. The skilled person will have no difficulties in testing functionality with regard to abiotic stresses such as heat.

The term "gene" means a DNA sequence comprising a region (transcribed region), which is transcribed into an RNA molecule (e.g. an mRNA) in a cell, operably linked to suitable regulatory regions (e.g. a promoter). A gene may thus comprise several operably linked sequences, such as a promoter, a 5' leader sequence comprising e.g. sequences involved in translation initiation, a (protein) coding region (cDNA or genomic DNA) and a 3' non-translated sequence comprising e.g. transcription termination sequence sites.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER; Gribskov, M. and Devereux, J., eds., M Stockton Press, New York, 1991). While a number of methods exist to measure identity between two polynucleotide or polypeptide sequences, the term "identity" is well known to skilled artisans (Carillo, H., and Lipton, D., SIAM J. Applied Math (1988) 48:1073). Methods commonly employed to determine identity or similarity between two sequences include, but are not limited to, those disclosed in GUIDE TO HUGE COMPUTERS, Martin J. Bishop, ed., Academic Press, San Diego, 1994, and Carillo, H., and Lipton, D., SIAM J. Applied Math (1988) 48:1073. Methods to determine identity and similarity are codified in computer programs. Preferred computer program methods to determine identity and similarity between two sequences include, but are not limited to, GCS program package (Devereux, J., et al., Nucleic Acids Research (1984) 12(1):387), BLASTP, BLASTN, FASTA (Atschul, S. F. et al., J. Molec. Biol. (1990) 215:403).

As an illustration, by a polynucleotide having a nucleotide sequence having at least, for example, 95% "identity" to a reference nucleotide sequence encoding a polypeptide of a certain sequence it is intended that the nucleotide sequence of the polynucleotide is identical to the reference sequence except that the polynucleotide sequence may include up to five point mutations per each 100 nucleotides of the reference polypeptide sequence. In other words, to obtain a polynucleotide having a nucleotide sequence at least 95% identical to a reference nucleotide sequence, up to 5% of the nucleotides in the reference sequence may be deleted and/or substituted with another nucleotide, and/or a number of nucleotides up to 5% of the total nucleotides in the reference sequence may be inserted into the reference sequence. These mutations of the reference sequence may occur at the 5' or 3' terminal positions of the reference nucleotide sequence, or anywhere between those terminal positions, interspersed either individually among nucleotides in the reference sequence or in one or more contiguous groups within the reference sequence.

Similarly, by a polypeptide having an amino acid sequence having at least, for example, 95% "identity" to a reference amino acid sequence of SEQ ID NO: 1 is intended that the amino acid sequence of the polypeptide is identical to the reference sequence except that the polypeptide sequence may include up to five amino acid alterations per each 100 amino acids of the reference amino acid of SEQ ID NO: 1. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

A nucleic acid according to the present invention may include any polymer or oligomer of pyrimidine and purine bases, preferably cytosine, thymine, and uracil, and adenine and guanine, respectively (See Albert L. Lehninger, *Principles of Biochemistry*, at 793-800 (Worth Pub. 1982) which is herein incorporated by reference in its entirety for all purposes). The present invention contemplates any deoxyribonucleotide, ribonucleotide or peptide nucleic acid component, and any chemical variants thereof, such as methylated, hydroxymethylated or glycosylated forms of these bases, and the like. The polymers or oligomers may be heterogenous or homogenous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the DNA sequences being linked are typically contiguous and, where necessary to join two protein encoding regions, contiguous and in reading frame so as to produce a "chimeric protein". A "chimeric protein" or "hybrid protein" is a protein composed of various protein "domains" (or motifs) which is not found as such in nature but which a joined to form a functional protein, which displays the functionality of the joined domains. A chimeric protein may also be a fusion protein of two or more proteins occurring in nature. The term "domain" as used herein means any part(s) or domain(s) of the protein with a specific structure or function that can be transferred to another protein for providing a new hybrid protein with at least the functional characteristic of the domain.

"Plant" refers to either the whole plant or to parts of a plant, such as cells, tissue or organs (e.g. pollen, seeds, gametes, roots, leaves, flowers, flower buds, anthers, fruit, etc.) obtainable from the plant, as well as derivatives of any of these and progeny derived from such a plant by selfing or crossing. "Plant cell(s)" include protoplasts, gametes, suspension cultures, microspores, pollen grains, etc., either in isolation or within a tissue, organ or organism.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. Optionally the term "promoter" includes herein also the 5' UTR region (5' Untranslated Region) (e.g. the promoter may herein include one or more parts upstream (5') of the translation initiation codon of a gene, as this region may have a role in regulating transcription and/or translation. A "constitutive" promoter is a promoter that is active in most tissues under most physiological and developmental conditions. An "inducible" promoter is a promoter that is physiologically (e.g. by external application of certain compounds) or developmentally regulated. A "tissue specific" promoter is only active in specific types of tissues or cells. A "promoter active in plants or plant cells" refers to the general capability of the promoter to drive transcription within a plant or plant cell. It does not make any implications about the spatio-temporal activity of the promoter.

The terms "protein" or "polypeptide" are used interchangeably and refer to molecules consisting of a chain of amino acids, without reference to a specific mode of action, size, 3 dimensional structure or origin. A "fragment" or "portion" of a protein may thus still be referred to as a "protein". An "isolated protein" is used to refer to a protein which is no longer in its natural environment, for example in vitro or in a recombinant bacterial or plant host cell.

A "genetically modified plant" refers herein to a plant or plant cell having been transformed, e.g. by the introduction of a mutation in an endogenous gene or part there of such that expression is enhanced, or by the introduction of an exogenous gene or additional copy or copies of an endogenous gene, said exogenous gene or additional endogenous gene may be integrated into the genome. A transgenic plant cell transformed with an (isolated) polynucleotide sequence and plant cells and plants regenerated therefrom, are all understood to comprise said (isolated) polynucleotide sequence. A transgenic plant cell may refer to a plant cell in isolation or in tissue culture, or to a plant cell contained in a plant or in a differentiated organ or tissue, and both possibilities are specifically included herein. Hence, a reference to a plant cell in the description or claims is not meant to refer only to isolated cells or protoplasts in culture, but refers to any plant cell, wherever it may be located or in whatever type of plant tissue or organ it may be present. Methods for obtaining transgenic plant cells and plants are well known in the art and include but are not limited to *Agrobacterium*-mediated transformation of plant explants, particle bombardment of plant explants, transformation of plant explants using whiskers technology, transformation using viral vectors, electroporation of plant protoplasts, direct uptake of DNA by protoplasts using polyethylene glycol, microinjection of plant explants and/or protoplasts. *Agrobacterium*-mediated transformation is a preferred method to introduce the nucleic acid molecule of the invention into plant explants. *Agrobacterium tumefaciens* harbors a natural vector called Ti plasmid which was engineered to make it suitable for introduction of exogenous nucleic acid molecules into plant genomes. For genetic transformation, plant-derived explants are incubated with suspension of *Agrobacterium* cells followed by cultivation of the explants on the medium containing a selective agent that promotes growth and regeneration of the transformed cells only.

DETAILED DESCRIPTION OF THE INVENTION

After persistent studies, the present inventors, by using the chip technique in developing plant heat-resistance genes, have isolated for the first time a new plant heat-resistance gene from *Brassica* spp., which can be used to improve the heat-resistance in a plant. The isolated gene is named as "BccJAZ5a", based on which, transgenic plants with improved heat resistance can be produced.

There is no specific limitation on the plants that can be used in the present invention, as long as the plant is suitable to be transformed by a gene. The plants include various crops, flower plants or plants of forestry, etc. Specifically, the plants include, but are not limited to, dicotyledon, monocotyledon or gymnosperm. More specifically, the plants include, but is not limited to, wheat, barley, rye, rice, corn, sorghum, beet, apple, pear, plum, peach, apricot, cherry, strawberry, *Rubus swinhoei* Hance, blackberry, bean, lentil, pea, soy, rape, mustard, opium poppy, *olea europea, helianthus*, coconut, plant producing castor oil, cacao, peanut, calabash, cucumber, watermelon, cotton, flax, *cannabis*, jute, citrus, lemon, grapefruit, spinach, lettuce, asparagus, cabbage, *Brassica campestris* L. ssp. *Pekinensis, Brassica campestris* L. ssp. *chinensis*, carrot, onion, murphy, tomato, green pepper, avocado, *cassia*, camphor, tobacco, nut, coffee, aubergine, sugar cane, tea, pepper, grapevine, nettle grass, banana, natural rubber tree and ornamental plant, etc.

The term "plant(s)" includes, but is not limited to, plants of Cruciferae, Gramineae and Rosaceae. For example, the "plant" includes but is not limited to *Brassica campestris* L. ssp. *Pekinensis* and *Brassica campestris* L. ssp. *chinensis* of *Brassica* spp. of the Cruciferae; *Abrabidopsis* spp. plant of the Cruciferae; rice of Gramineae; and tobacco, melon and fruit, vegetable, rape and the like. More preferably, the "plant" is a plant of the *Brassica* spp. or *Abrabidopsis* spp. of the Cruciferae.

As used herein, the term "isolated" means that a substance has been separated from the original or native environment where it is initially found. For example, a polynucleotide and a polypeptide in a natural state in the living cell is not isolated or purified. However, when the same polynucleotide or polypeptide is separated from the other substances that coexist in the said natural state, it is called "isolated" and/or "purified".

As used herein, the "isolated plant heat-resistance protein (polypeptide)", "isolated polypeptide that improves the plant heat-resistance", "isolated BccJAZ5a protein" or "isolated BccJAZ5a polypeptide" refers to the BccJAZ5a protein substantially free of the other proteins, lipids, saccharides and other substances that are naturally associated with said protein. A skilled person in the art can utilize the standard protein purification technique to purify the BccJAZ5a protein. The substantially pure polypeptide may form a single major band on a non-reduced polyacrylamide gel.

As used herein, the term "comprising", "having" or "containing" includes "comprising", "consisting substantively of", "consisting essentially of", and "consisting of". The "consisting substantively of", "consisting essentially of" and "consisting of" are specific concepts of the generic terms "comprising", "having" and "containing".

The polypeptide of the present invention can be a recombinant polypeptide, a natural polypeptide or a synthetic polypeptide. Preferably, it is a recombinant polypeptide. The polypeptide of the present invention can be a product purified from a natural source, chemically synthesized, or recombinantly produced by prokaryotic or eukaryotic hosts (such as, bacterium, yeast, higher plant, insect and mammalian cell). Depending on the host used in recombinant production, the polypeptide of the present invention can be glycosylated or non-glycosylated. The polypeptide of the current invention can further include or not include the first native methionine residue.

The present invention further includes fragments, derivatives and analogs of the BccJAZ5a protein. As used herein, the terms "fragment", "derivative" and "analog" refer to the polypeptide that have substantially the same biological function and/or activity of the BccJAZ5a protein of the present invention. The polypeptide fragment, derivative or analog of the present invention may be (i) a polypeptide in which one or several conservative (preferred) or non-conservative amino acid residues are substituted by one or more amino acid residues that are genetically encoded or not, or (ii) a polypeptide with one or more amino acid residues bearing a substituent, or (iii) a fusion polypeptide of the mature polypeptide and another compound (such as a compound for extending the half life of the polypeptide, such as polyethylene glycol), or (iv) a polypeptide formed by an additional amino acid sequence (such as a leader sequence or a secretion sequence, or a sequence facilitating purification, or a proteinogenic sequence, or a fusion protein) fusing to the polypeptide sequence.

According to the definitions provided herein, these fragments, derivatives and analogs are understood by a person skilled in the art.

As used herein, the term "BccJAZ5a protein" refers to a polypeptide providing improved heat resistance based on the sequence of SEQ ID NO:4. This also includes the variants of SEQ ID NO:4 that exhibit improved plant heat resistance. Mutations include but are not limited to deletion, insertion and/or substitution of one or more (generally 1-50, preferably 1-30, more preferably 1-20, most preferably 1-10, further more preferably 1-8 or 1-5) amino acids, and addition or deletion of one or more (generally within 20, preferably within 10, more preferably within 5) amino acids at the C-terminus and/or N-terminus. For example, it is understood that substitution with an amino acid residue having close or similar property will generally not affect the function of the protein. Further, for example, addition or deletion of one or more amino acids from the C-terminus and/or N-terminus will generally not affect the function of the protein. The term also includes the active fragments and active derivatives of the BccJAZ5a protein.

Variants of the polypeptide includes its homologous sequence, conservative mutants, allelic mutant, natural mutant, induced mutant, protein encoded by a DNA that could hybridize to the DNA of BccJAZ5a protein under a high or low stringent condition, and polypeptide or protein obtained by utilizing an anti-serum against the BccJAZ5a protein. The present invention also provides more related polypeptides, such as fusion proteins containing BccJAZ5a protein or fragments thereof. In addition to the full-length or almost full-length polypeptides, the present invention also includes the soluble fragments of the BccJAZ5a protein. Generally, the fragment contains at least about 20, generally at least about 30, preferably at least about 50, more preferably at least about 80, most preferably at least about 100 continuous amino acid of the BccJAZ5a protein.

The present invention also provides analogs of the BccJAZ5a protein or polypeptide. These analogs may be different from the native BccJAZ5a protein in the primary sequence or in modification patters along the same primary sequence, or both. These polypeptides include the natural or induced genetic mutants. The induced mutants may be obtained via various techniques, for example, by radiation or by exposure to a mutagen so as to produce a random mutagenesis. They may also be obtained by site-directed mutagenesis or some other known biological technologies. The analogs also include those having residues different from the natural L-amino acid (such as D-amino acid), and those having unnatural or synthetic amino acid(s), such as β- and γ-amino acids. It should be understood that the polypeptide of the subject invention is not limited to the above representative examples. Modification patterns, which will not change the primary structure, include in vivo or in vitro chemical derivation, such as acetylation or carboxylation. Modification may also be glycosylation. Modification may also be phosphorylation of the amino acid residues (such as, phosphorylated tyrosine, phosphorylated serine, and phosphorylated threonine) in the sequence. Also included are polypeptides which are modified to have an improved anti-proteolysis property or optimize the solubility property.

In the present invention, "a conservative mutant of BccJAZ5a protein" refers to a polypeptide having up to 20, preferably up to 10, more preferably up to 5, most preferably up to 3 amino acids in the amino acid sequence of SEQ ID NO:4 being replaced by amino acids with similar properties. These mutant polypeptides may be produced according to the amino acid replacement shown below in Table 1.

TABLE 1

| Amino acid residue | Representative substitution | Preferred substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The present invention further provides polynucleotide sequences encoding the BccJAZ5a protein of the current invention or conservative variant polypeptides thereof.

The polynucleotides of the present invention may be DNA or RNA molecules. The DNA molecules include cDNA, genomic DNA and synthetic DNA. The DNA molecules may be in the form of a single strand or of double strands. The DNA molecule may be the coding strand or the non-coding strand. The coding sequence encoding the mature polypeptide may be identical to the coding sequence of SEQ ID NO: 1 or 2, or may be their degeneration variants. As used therein, "a degeneration variant" refers to a nucleic acid molecule that encodes a protein having the sequence of SEQ ID NO: 4 with a nucleotide sequence different from the coding sequence as set forth in SEQ ID NO: 1 or 2.

The polynucleotides encoding the polypeptide of SEQ ID NO:4 may comprise a coding sequence only encoding the polypeptide; a coding sequence of polypeptide and an additional coding sequence; the coding sequence of the polypeptide and a non-coding sequence, optionally as well as an additional coding sequence.

The term "polynucleotide encoding a polypeptide" may optionally include, in addition to the polynucleotide encoding said polypeptide, an additional coding and/or a non-coding polynucleotide.

The present invention further relates to variants of the above polynucleotides, which encode the same amino acid sequence of the polypeptide of the present invention, and fragments, analogs and derivatives thereof. The variants of the polynucleotides may be the naturally occurring allelic mutants or non-naturally occurring mutants. The nucleotide variants include substitution variants, deletion variants and insertion variants. As known in the prior art, an allelic variant is an alternative form of a polynucleotide, wherein the mutation may be substitution, deletion or insertion of one or more nucleotides, but the function of the polypeptide encoded by the allelic variant is substantively un-altered.

The present invention also relates to a polynucleotide hybridizing to any of the above sequences and having at least 50%, preferably at least 70%, more preferably at least 80% sequence identity between the two sequences. The present invention specifically relates to a polynucleotide hybridizing to the polynucleotides of the present invention under stringent conditions. In the present invention, the "stringent condition" refers to: (1) hybridization and elution at a relatively lower ionic strength and relatively higher temperature, such as 0.2×SSC, 0.1% SDS, 60° C.; or (2) presence of denaturation agent during hybridization, such s 50% (v/v) formamide, 0.1% calf serum/0.1% Ficoll, 42° C., and the like; or (3) conditions only allowing hybridization between two sequences that have at least 80%, preferably at least 90%, more preferably at least 95% identity. Moreover, the polypeptide encoded by the hybridizing polynucleotide exhibits the same biological function and activity as those of the mature polypeptide as shown in SEQ ID NO: 4.

The present invention also relates to nucleic acid fragments that can hybridize to the any of the above sequences. As used herein, a "nucleic acid fragment" contains at least 15 nucleotides, preferably at least 30 nucleotides, more preferably at least 50 nucleotides, most preferably at least 100 nucleotides. The fragment of nucleic acid may be used in the amplification technique of nucleic acid (such as PCR) to determine and/or isolate the polynucleotide encoding the BccJAZ5a protein.

The full-length nucleotide sequence of the BccJAZ5a protein of the present invention or fragment thereof can typically be prepared via PCR amplification method, recombinant method or artificial synthesis. As to PCR amplification, the sequences of interests can be amplified by designing primers according to the related nucleotide sequence disclosed in the present invention, e.g. the open-reading frame, and using a commercially available cDNA library or a cDNA library prepared according to any of the conventional methods known in the art as a template. For a large sequence, typically, two or more PCR amplifications may be needed, the fragments thus obtained in each amplification may be fused together, e.g. ligated, in a correct orientation.

Once the related sequence is obtained, it can be produced in a large amount using recombinant techniques. The sequence may be cloned into a vector. The vector may be transformed into a cell, and then the sequence can be isolated from the proliferated host cells using conventional means.

Furthermore, the related sequence can be synthesized by artificial synthesis, e.g. when the fragment is relatively short. Several small fragments may be first synthesized and then fused, e.g. via fusion PCR or ligation, into a long fragment.

The DNA sequence encoding the protein (or fragment or derivative thereof) of the present invention can be prepared completely via chemical synthesis. The obtained DNA sequence can be incorporated into various known DNA molecules (such as vectors) and then into cells. Further, mutations may be introduced into the protein sequence of the present invention through the chemical synthesis.

The present invention also relates to a vector containing the polynucleotide of the present invention, a host cell genetically engineered to contain the vector or the coding sequence of the BccJAZ5a protein of the present invention, and a method for recombinantly producing the polypeptide of the present invention.

The polynucleotide of the present invention can be used to express or produce a recombinant BccJAZ5a protein using conventional recombinant DNA techniques. The following steps may be included in such a use:

(1) Transforming or transfecting a host cell with a polynucleotide (or its variant) encoding the BccJAZ5a protein of the present invention, or a recombinant expression vector containing said polynucleotide;

(2) culturing the host cell in a culture medium;

(3) isolating and purifying the protein from the culture medium or the cultured cells.

In the present invention, the polynucleotide sequence of the BccJAZ5a protein can be inserted into a recombinant expression vector. The term "recombinant expression vector" refers to a bacterial plasmid, phage, yeast plasmid, plant cell virus, mammalian cell virus and any other vectors known in the art. Any plasmids and vectors can be used as long as they can replicate and retain stably in the host. Expression vectors may comprise a replication origin, promoter, markers and/or translation control element.

Various methods known in the art can be used to construct an expression vector containing a DNA sequence encoding the BccJAZ5a protein and suitable transcription/translation regulatory signals. These methods include in vitro recombinant techniques, DNA synthesis, in vivo recombinant techniques, etc. The DNA sequence may be operably linked under a suitable promoter for directing mRNA synthesis in the expression vector. The expression vector can further include a ribosome binding site for initiating the translation and a transcription terminator.

Further, the expression vector may contain one or more selectively labeled genes to provide phenotypic traits for selecting the transformed host cells. The labeled genes may encode, for example, dihydrofolate reductase, neomycin resistance and green fluorescent protein (GFP) for culture of eukaryotic cells, and kanamycin or ampicillin resistance for *E. coli*.

The vector containing the above suitable DNA sequence and suitable promoter or regulatory sequence can be used to transform suitable host cells for protein expression.

The host cell may be a prokaryotic cell, such as bacterial cell; or lower eukaryotic cell, such as yeast cell; or higher eukaryotic cell, such as plant cell. Examples include *E. coli, Streptomyces, agrobacterium*, fungi cell such as yeast, and plant cell, etc.

When expressing the polynucleotide of the present invention in a higher eukaryotic cell, the transcription may be enhanced when an enhancer sequence is inserted into the vector. TAn enhancer may be a cis-acting factor of DNA, which may contain about 10 to 300 bp and can act on a promoter to enhance the transcription of the gene.

A person skilled in the art knows how to select a vector, promoter, enhancer and host cell. Transformation of a host cell with the recombinant DNA can be carried out using conventional techniques known by the person skilled of the art. When the host cells are prokaryotic cells, such as *E. coli*, competent cells that can uptake the DNA can be harvested after the exponential growth phase and then treated by $CaCl_2$ method, well described in the art. Another method is to use $MgCl_2$. If desired, the transformation could be conducted using electroporation. When the host cell is of an eukaryotic origin, one or more of the following DNA transfecting methods may be used: calcium phosphate precipitation, conventional mechanical method such as microinjection, electroporation, liposome packing, etc. Transformation of plant may also be achieved by using *agrobacterium* or gene gun transformation, and the like, such as leaf discs transformation, rice immature embryo transformation, etc. The transformed plant cell, tissue or organ can be regenerated into a plant via conventional methods, so as to obtain a plant having altered traits.

The transformant can be cultured in conventional ways to express the polypeptide encoded by the gene of the present invention. Depending on the host cell used, the culture medium used for the culture may be selected from various conventional culture mediums. Culturing is carried out under conditions suitable for growth of the host cell. When the host cell grows to a suitable density, the selected promoter may be induced by a suitable method (such as temperature change or chemical induction), after which the cells may be further cultured for a period of time.

In the above methods, the recombinant polypeptide can be expressed in the cell, or on the cell membrane, or be secreted outside the cell. If desired, the recombinant protein could be isolated and purified via various isolation methods by utilizing the physical, chemical or other properties of the protein. These methods are well known in the art. Examples include but are not limited to the conventional renaturation treatment, treatment with protein precipitant (such as salting out), centrifugation, osmosis (for disrupting the bacterium), ultra-treatment, ultra-centrifugation, molecular sieve chromatography (gel filtration), adsorption chromatography, ion-exchange chromatography, liquid chromatography such as high performance liquid chromatography (HPLC) and the other, and combinations thereof.

The recombinant BccJAZ5a can be used in many applications. For example, it can be used to screen for the antibody, polypeptide or the other ligands agonistic or antagonistic to the function of the BccJAZ5a protein. Screening a polypeptide library with the expressed recombinant BccJAZ5a protein may help finding valuable polypeptide molecules that could inhibit or stimulate the function of the BccJAZ5a protein.

The whole polynucleotide of the present invention or a portion thereof can be used as a probe, which may be fixed onto a microarray or a DNA chip (also termed as "gene chip") to perform an analysis of gene differential expression. Primers specific for the BccJAZ5a protein to perform RNA reverse transcription polymerase chain reaction (RT-PCR) for in vitro amplification can also be used to detect the transcription products of the BccJAZ5a protein.

The present invention also relates to a method for modifying a plant (to improve the heat resistance of the plant), comprising enhancing the expression of the BccJAZ5a gene and/or the activity of encoded protein in the plant.

Methods for enhancing the expression of the BccJAZ5a gene are well known in the art. For example, plants can be transformed with an expression construct carrying the BccJAZ5a coding gene to over-express the BccJAZ5a gene. A promoter can be used to enhance the expression of the BccJAZ5a gene. An enhancer (such as the first intron of the rice waxy gene or the first intron of the Actin gene, and the like) can be used to enhance the expression of the BccJAZ5a gene. Promoters include but are not limited to the 35S promoter, and the Ubi promoter in rice and corn.

In one embodiment of the present invention, a method for obtaining a plant with enhanced expression of BccJAZ5a protein includes:

(1) providing an *agrobacterium* strain containing an expression vector, wherein the expression vector contains the DNA coding sequence of the BccJAZ5a protein;
(2) contacting a plant cell, tissue or organ with the *agrobacterium* of step (1) such that the DNA coding sequence of the BccJAZ5a protein is transformed into the plant cell and integrated into the chromosome;
(3) selecting the plant cell or tissue transformed with the DNA coding sequence of the BccJAZ5a protein; and
(4) regenerating the plant cell or tissue of step (3) into a plant.

Any suitable conventional means, including reagents, temperature and pressure controls, can be used in this process.

The present invention also includes agonists to the BccJAZ5a protein or its coding gene. Since the agonists of the BccJAZ5a protein can regulate the activity or expression of the BccJAZ5a protein, the said agonists can also enhance the heat resistance of a plant through affecting the BccJAZ5a protein, such that traits are improved.

The agonists of the BccJAZ5a protein refer to any substance that can enhance the activity of BccJAZ5a, maintain the stability of BccJAZ5a, promote the expression of BccJAZ5a, prolong effect duration of BccJAZ5a, or promote transcription and translation of BccJAZ5a. These substances can be used in the present invention as agents for enhancing the heat resistance of plant.

In an embodiment of the present invention, a BccJAZ5a gene is provided, the genomic sequence of which is listed in SEQ ID NO: 1, and the CDS sequence of which is indicated in SEQ ID NO: 2. Said gene encodes a protein containing 270 amino acids (SEQ ID NO:4). Said BccJAZ5a gene provides a new route for modification of tolerance of a plant.

The present invention will be further illustrated in combination with the examples below. It should be understood that these examples are for illustrating the present invention, but not be understood to limit the scope of the present invention in any way. The experimental methods, wherein specific conditions are not indicated in the following examples are performed using conventional conditions, such as those described in Sambrook et al., Molecular Cloning: A Laboratory Manual (New York: Cold Spring Harbor Laboratory Press, 2002), or according to the conditions recommended by the manufacturer. Unless otherwise specifically indicated, the percentage and part are calculated based on weight. Unless otherwise specifically indicated, all of the scientific terms used herein have the same meanings as those familiar to the skilled in the art. Furthermore, any methods and materials equivalent to the disclosed contents can be used in the present invention. The preferred practicing method and material disclosed herein are just for illustrative purpose.

EXAMPLES

I. Materials and Methods

Materials

HR seeds of heat-resistance *Brassica campestris* L. ssp. *chinensis* (Bcc), HS seeds of temperature-sensitive *Brassica campestris* L. ssp. *chinensis* (Bcc), Seeds of *Brassica campestris* L. ssp. *Pekinensis* (Bcp) 99Bre and CHIFU variety of *Brassica campestris* L. ssp. *Pekinensis* were obtained from Shanghai Agricultural Science and Technology Seed, LLC. Col is the wild type of *Arabidopsis thaliana* obtained from Institute of Genetics and Developmental Biology, Chinese Academy of Sciences.

Total RNA Extraction from Plant Tissue

Reagent: Extraction Kit of TaKaRa RNAiso Reagent.

Steps:

a) Well grinding the materials in liquid nitrogen, adding an extraction buffer into the sample in an amount of 100 mg of material per ml extraction buffer, mixing to even, and then standing at room temperature for 10 minutes.

b) Centrifuging at 13000 rpm for 5 min, transferring the supernatant into a new centrifuge tube, adding 200 μl chloroform, mixing to even, and then standing at room temperature for 10 minutes to allow for phase separation.

c) Centrifuging at 13000 rpm for 5 min, and carefully pipetteing the supernatant into a new centrifuge tube.

d) Adding isopropanol in an equal volume, standing at room temperature for 10 minutes after well mixing.

e) Centrifuging at 13000 rpm for 5 min, discarding the supernatant and washing once with 1 ml of 75% (v/v) ethanol.

f) Centrifuging at 7800 rpm for 5 min, discarding the supernatant and centrifuging again at a low speed; removing the residual liquid with a tip; air drying at room temperature; adding a suitable amount of water free of RNase upon the RNA becomes dry; allowing for thorough dissolution at 65° C. for 10 min; and then storing at −70° C.

Semi-Quantitative RT-PCR

Primers used in the RT-PCT include:

```
BccJAZ5a:
Forward:
                                    (SEQ ID NO: 5)
5' AAGAAGCCAAGTCTGTGA 3';

Reverse:
                                    (SEQ ID NO: 6)
5' TCGGAGGATAATGATGAC 3'.

BccJAZ5b:
Forward:
                                    (SEQ ID NO: 7)
5' GCTAAACGGAAAGACAGAGC 3';

Reverse:
                                    (SEQ ID NO: 8)
5' TGAGGGAGACGAGGACAAG 3'.

BccLOX3:
Forward:
                                    (SEQ ID NO: 9)
5' TCTAATATGGTCCGCAATC 3';

Reverse:
                                   (SEQ ID NO: 10)
5' TTTCAATCCGTCCAATCT 3'.

AtJAZ5:
Forward:
                                   (SEQ ID NO: 11)
5' AAAATGCTAAGGCACAAG 3';

Reverse:
                                   (SEQ ID NO: 12)
5' GATGAGGTAGAGGGTTCG 3'.

BccUBQ.5:
Forward:
                                   (SEQ ID NO: 13)
5' TCCGTCCACCTTGTAGAACTG 3';

Reverse:
                                   (SEQ ID NO: 14)
5' TGAAAACCCTAACGGGGAAA 3'.

ACTIN:
Forward:
                                   (SEQ ID NO: 15)
5' TGGCATCAYACTTTCTACAA 3';

Reverse:
                                   (SEQ ID NO: 16)
5' CCACCACTDAGCACAATGTT 3'.
```

Reagents:

AMV reverse transcriptase (TAKARA);

RNase inhibitor (TAKARA);

DNase I (RNase free) (TAKARA).

Steps:

a) Respectively extracting the total RNA from leaves of *Brassica campestris* L. ssp. *chinensis* after different heat treatments; treating with DNase I (RNase free) for 30 min, and then extracting by phenol-chloroform; precipitating, blow-drying, dissolving in water free of RNase.

b) Determining OD260 values and quantifying by electrophoresis, taking 1 μg total RNA for reaction at 42° C. for 1 hour and 94° C. for 5 min to inactivate the reverse transcriptase according to standard instructions.
c) Diluting the reverse transcripts into double volume, taking 1 µl of each to perform PCR. The PCR reaction conditions are as follows: 94° C. 3 min; 94° C. 30 sec, 55° C. 30 sec, 72° C. 30 sec, 25-28 cycles; 72° C. 5 min. For the calibration of the template amounts in the RT-PCR, the primers of Ubiquitin (BccUBQ5) and Actin are used as an internal control in a parallel PCR reaction.

Extraction of Total Plant DNA by CTAB Method

Reagents:

2×CTAB buffer (100 ml): 10 ml 1M Tris pH 8.0; 4 ml 0.5 M EDTA pH8.0; 8.19 g NaCl; 2 g CTAB; 1 g PVP K30; qs to 100 ml.

1×CTAB buffer (100 ml): 5 ml 1M Tris pH 8.0; 2 ml 0.5 M EDTA pH8.0; 1 g CTAB; qs to 100 ml.

High-salt TE (100 ml): 1 ml 1M Tris pH 8.0; 200 p10.5 M EDTA pH8.0; 5.844 g NaCl; qs to 100 ml.

10% (w/v) CTAB (50 ml): 5 g CTAB; 2.045 g NaCl; qs to 100 ml.

Steps:
a) Grinding 5 g plant materials in liquid nitrogen into powder and then transferring into a 40 ml centrifuge tube.
b) Adding into the tube 15 ml 2×CTAB buffer (1:1) which has been pre-heated at 65° C., incubating at 65° C. for 10 min after well mixing, turning upside down for several times during incubation.
c) Adding one volume of chloroform: isoamyl alcohol (24:1), centrifuging at 11000 rpm for 5 min after uniformly mixing.
d) Pipetteing the supernatant to a new centrifuge tube and adding 1/10 volume of 10% CTAB, and then adding one volume of chloroform: isoamyl alcohol, centrifuging for 5 min after uniformly mixing.
e) Removing the supernatant, repeating step d) for 2-3 times, and then transferring the supernatant to a new centrifuge tube, adding more than 2 volumes of precipitation buffer (1×CTAB), gently mixing to form a uniform solution, standing at room temperature for 30 min.
f) Centrifuging and harvesting the precipitate, re-suspending the precipitate in 5 ml high-salted TE at 65° C., (a few RNase may optionally be added), incubating at 37° C. for 30 min.
g) Centrifuging at 11000 rpm for 10 min, and then transferring the supernatant to a new 1.5 ml centrifuge tube.
h) Adding thereinto 2 volumes of anhydrous ethanol, after uniformly mixing, placing at −20° C. for 30 min; centrifuging, discarding the supernatant, washing with 70% ethanol and then air-drying, dissolving in 100 µl TE.

Construction of a Vector: 35S::BccJAZ5a Genomic DNA

Primers used for amplifying BccJAZ5a DNA from the genomic DNA are as follows:

```
Forward:
                                   (SEQ ID NO: 17)
5' CTTTCTTCCATTTGACGC 3';

Reverse:
                                   (SEQ ID NO: 18)
5' CTGCAACTAAATTCACTATTG 3'.
```

Steps:
a) Isolating the genomic fragment of BccJAZ5a by PCR from the total genomic DNAs of Brassica campestris L. ssp. chinensis.
b) Cleaving the fragment with Kpn I, cloning the fragment into pCAMBIA1300 vector (the starting pCAMBIA1300 vector was obtained from CAMBIA Corporation) (the PCR product was linked between the 35S and Nos). Because it was cleaved by one enzyme, there can be ligations in two orientations (forward and reverse). Therefore, sequencing was performed for verification.
c) Transforming the vector of pCAMBIA1300-DREB2A containing the gene in the forward orientation into the strain of agrobacterium GV3101 (Invitrogen) by freeze-thawing transformation, and confirming by PCR.

Preparation of Competent Agrobacterium Cells and Transformation by Freeze-Thawing Method a) A single GV3101 clone was picked up from the fresh plate cultured at 28° C. for 48 hours and transferred to 20 ml LB liquid culture medium (rif 50 mg/l, GM 50 50 mg/l), and then cultured overnight at 28° C. by shaking at 250 rpm (the concentration should not be too high). (All the following operations were conducted in an aseptic condition).
b) The strain solution of step a) was placed in an ice-bath for 20 min and then separated into aliquots in 5 ml centrifuge tubes (4 ml per tube). The tubes were placed on an ice-bath for 10 min.
c) The tubes were centrifuged at 4000 rpm (5-10° C.) for 10 min and the supernatant was discarded.
d) 20 mM of pre-cooled $CaCl_2$ were added into each tube to re-suspend the strain pellets. The tubes were placed in an ice-bath for 10 min.
e) The tubes were centrifuged at 4000 rpm (5-10° C.) for 10 min and the supernatants were discarded.
f) 300µl of 20 mM $CaCl_2$ (depending on the concentration of the strains) was added into each tube. The solutions in the tubes were pooled into a 1.5 ml centrifuge tube.
g) 1 µl of plasmid or all ligated products were added into the tubes, and the tubes were placed in an ice-bath for 5 min. After that, the tubes were placed into liquid nitrogen for 4-5 min.
h) The tubes were placed at 37° C. for 5 min. Then 400 µl LB culture medium was added into each tube and the tubes were incubated at 28° C. for 2 hours to revive the bacteria and to express the appropriate antibiotics resistance genes.
i) 200 µl of solution were taken from each tube and plated, the plates were kept at room temperature for adaption, and then cultured at 28° C.

Transformation of Arabidopsis thaliana (L.) Heynh by a Floral-Dip Method and Screening Reagents:
Transformation buffer (1 L): major elements (50×): 10 ml; trace elements (1000×): 0.5 ml; $CaCl_2$ (100×): 5 ml; iron salt (200×): 2.5 ml; organic (100×): 10 ml; sucrose: 50 g; 6-BA (1 mg/ml): 10 µl; Silwet L-77: 400 µl (if used in vacuum leaching, 200 µl); adjusted to pH 5.8 using KOH, qs to 1 L.

Culture plate for screening: 3% (w/v) sucrose MSO solid culture medium (pH5.8), kanamycin (Kan) was added to a concentration of 50 mg/l (for Nossen background screening in Arabidopsis thaliana (L.) Heynh).

Steps:
a) Transformation was conducted when the stem of Arabidopsis thaliana (L.) Heynh has reached 5 cm in height after bolting. For plants with a low fruition rate, transformation is to be conducted 4 days after topping.
b) Before transformation, the pollinated flowers and silicle were cleaned out, and the soil is allowed to adsorb water overnight.
c) An overnight culture of Agrobacterium was diluted in the culture medium at a ratio of 1:100 in a big flask. After culturing at 28° C. for 24 hours, the medium was centrifugated at 5000 rpm and 4° C. The supernatant was discarded. The *agrobacterium* pellets were re-suspended in the transformation buffer at an amount of two volumes of the strain stock solution to provide an OD600 of about 0.8.

d) The overground of *Arabidopsis* was completely soaked into the strain solution for 30 sec, and then taken out, wrapped by preservative film and newspaper and placed in dark overnight. In the next day, the plant part was transferred into a phytotrone for normal vertical culture. The seeds were harvested and dried for 2 weeks.

e) After sterilization, the seeds were spread on a MSO solid plate containing 50 mg/l Kan. After jarovization at 4° C. for two days, the plate was moved into a tissue culture chamber. The seedlings having Kan resistance were selected and transferred to grow in soil.

f) Genomic DNA was extracted from leaves. After PCR identification, the positive seedlings were obtained. A pure transgenic linkage was obtained via two further passages, which were used for further analysis.

Transformation of Cabbage by Vacuum Leaching and Screening (1) Transformation of *Brassica campestris* L. ssp. *Pekinensis* a) The *Brassica campestris* L. ssp. *Pekinensis* seeds were placed on filter paper wetted with water for jarovization at 4° C. for two months (a *Brassica campestris* L. ssp. *Pekinensis* plant will bolt and blossom during the young seedling period if the cabbage has been subjected to jarovization, this may facilitate the transformation). Then the seedling of *Brassica campestris* L. ssp. *Pekinensis*, the hypocotyls of which have elongated, was transferred to soil. At the time of bolting and the first blossom, transformation could be carried out. Before transformation, the soil was irrigated overnight.

b) The transformation solution containing *agrobacterium* was prepared according to the methods for transforming *Arabidopsis*.

c) The overground part of *Brassica campestris* L. ssp. *Pekinensis* was completely soaked into the strain solution, upside down. Then said part was placed in a dryer having a vacuum pump. The dryer was vacuumed 5 minutes×2 with an interval of 2 minutes, until the leaves become transparent. The dryer was aerated and the plant was taken out and placed horizontally, covered by preservative film and newspaper, and placed in dark overnight. The next day, the plant was transferred and planted into a big vase for culturing in the conventional way. During the blossom stage, pollination was manually performed on the buds, followed by having each bud pouched. Seeds were dried for 2 weeks after harvesting.

d) The sterilized seeds were dried on sterile filter paper. Then the seeds were transferred into a triangle flask containing culture medium containing Kan 50 mg/l. Jarovization was performed at 4° C. for 2-3 days. Then the flask was transferred into a thermostatic chamber for incubation.

e) Transformants of *Brassica campestris* L. ssp. *Pekinensis* were identified after euphylla develops. The transformant has green euphylla and normally developed root. On the contrary, the non-transformant has white euphylla and it does not have root. After the 3-4 leaves of euphylla develop from the transformant, the transformant was moved into soil after 3 days of acclimatization.

(2) Transformation of *Brassica campestris* L. ssp. *chinensis*

Similarly, *Brassica campestris* L. ssp. *chinensis* was transformed by vacuum leaching. The transformation method and conditions are identical to those used for *Brassica campestris* L. ssp. *Pekinensis*.

II. Examples

Example 1

Obtaining the Gene of Interest

Gene expression, especially functional genes' expression, in plant is temporally and/or spatially specific. The inventors detected the expression of functional genes in *Brassica campestris* L. ssp. *chinensis* specimens under different heat treatment conditions by hybridizing mRNAs extracted from specimens having been subjected to different heat treatments with a chip presenting all of the functional genes in *Brassica campestris* L. ssp. *chinensis*. Conventional methods for detecting gene expression require a large scale of sequencing, which can only detect a few gene expressions in one time with low detection sensitivity. Using gene chip technique allows for not only quantitatively and qualitatively determining gene expression level in a high sensitivity, but also studying expression of thousands of genes in one sample simultaneously. Gene chip technology enables not only to shorten the screening time, but also to obtain more stable and more pinpointed results. It is recommendable for its high adaptability and utility value. Further, AFLP (Amplified Fragment Length Polymorphism) is a recently developed molecular marker for selectively amplifying restrictive fragments. This method has been widely used in various fields, including genetic mapping in vegetables, analysis on genetic diversity and relationship, location of important genes, study on regulation of gene expression, genetic fingerprinting in vegetables and identification of purity of lineage, and molecular marker-assisted selection.

To satisfy the need for planting *Brassica campestris* L. ssp. *chinensis* in summer and autumn, the inventors of the present invention screened for and obtained a heat-resistance gene in cabbages using gene chip technology in combination with cDNA-AFLP technology. The inventors have also developed transgenic lines that expresses said gene.

The gene "BccJAZ5" obtained in the present invention has two copies, which respectively are BccJAZ5a (copy a) and BccJAZ5b (copy b). The genomic sequence of BccJAZ5a is indicated in SEQ ID NO:1, its CDS sequence is indicated in SEQ ID NO:2. It encodes a protein "BccJAZ5a" having 270aa (SEQ ID NO:4). The genomic sequence of BccJAZ5b is shown in SEQ ID NO:3.

Example 2

Detection of the Candidate Heat-Resistance Genes' Expression by RT-PCR after Heat Treatment In the cDNA-AFLP data, the jasmonate acid signal pathway was changed after heat treatment. The inventors of the present invention have studied two genes in this pathway. BccLOX3 is a jasmonate synthase and BccJAZ5 is a negatively correlated signal protein regulated by Ubiquitin modification. In the heat-sensitive variety, these two genes were strongly expressed as induced by heat treatment. See FIG. 1.

The cDNA-AFLP of the present invention shows that the expression of copy b exhibited significant change. The DNA sequence homology between copy a and copy b of CHIFU variety of *Brassica campestris* L. ssp. *Pekinensis* is 75.8%. However, the homology of the corresponding copies in the heat-resistance and heat-sensitive varieties is higher than 98%. The sequence alignment results can be found in Tables 2 and 3.

TABLE 2

| DNA sequence alignment among Bcc HR and HS varieties and Bcp CHIFU variety | | | |
|---|---|---|---|
| | BcpJAZ5a | BccJAZ5a HR line | BccJAZ5b HS line |
| BcpJAZ5b | 75.8% | | 99.7% |
| BccJAZ5b HR line | | | 98.8% |
| BccJAZ5a HS line | 100% | 99% | |

TABLE 3

| DNA sequence homology obtained by aligning AtJAZ5, BcpJAZ5a, BcpJAZ5b, and BccJAZ5b based on the cDNA-AFLP results | | | |
|---|---|---|---|
| | AtJAZ5 | BcpJAZ5a | BcpJAZ5b |
| BccJAZ5b | 50.3% | 40.8% | 99.7% |
| AtJAZ5 | — | 77.0% | 74.3% |
| BcpJAZ5a | — | — | 75.8% |

The inventors further demonstrated by RT-PCR that expression of both BccJAZ5b and BCCLOX3 was up-regulated under conditions of heat treatment. And this up-regulation was more significant in the heat-sensitive variety. See FIG. 2.

Example 3

Phenotype of the Transgenic Plant with the Heat-Resistance Gene

To determine the function of the heat-resistance gene, the inventors of the present invention constructed an expression plant vector 35S::BccJAZ5a that comprised the 35S promoter. This vector was used to transform *Arabidopsis*. Gene expression and heat resistance of the *Arabidopsis* T2 generation plant was detected.

The inventors have detected the exogenous BccJAZ5a and endogenous AtJAZ5a by RT-PCR. See the three transgenic lineages 35S::BccJAZ5a in FIG. 3. The expressions of BccJAZ5a in all transgenic plants were up-regulated. However, they did not show stronger heat-resistance as compared with the wild type plant. On the contrary, number 2 (2#) transgenic lineage showed the worst survival rate. The inventors found that expression of AtJAZ5a in the number 2 transgenic lineage was inhibited, which may result in low tolerance to heat. Subsequently, 2# showed obvious growth deficiency. The inventors further studied the phenotype of the T4 generation of the transgenic plant 35S::BccJAZ5a in the bolting stage. All three transgenic lineages showed improved heat resistance as compared with the wild type plant. This result was opposite to that obtained in the plants in seedling stage. Therefore, BccJAZ5a may exert a heat resistance function in the bolting stage. For example, because mechanisms in response to heat stress in the seedling stage and in the bolting stage are different. See FIG. 4.

Example 4

Phenotypes of the Plants of Transgenic *Brassica campestris* L. ssp. *Pekinensis* and *Brassica campestris* L. ssp. *chinensis* after Heat Treatment The inventors of the subject invention used a heat treatment system to verify the phenotypes of the plants of transgenic *Brassica campestris* L. ssp. *Pekinensis* and *Brassica campestris* L. ssp. *chinensis* after heat treatment. The seeds of the transgenic plants were accelerated to sprout and subjected to jarovization under low temperature, and then planted in a plastic culture bowl. The seedlings were cultured at 25° C. When bolting begun, the seedlings having consistent growth status were selected and placed in a culture box for heat treatment at an increased temperature. The temperature was set to 32° C., and the treatment lasted for 10 days. Then the temperature was switched back to 25° C. for 2 days. Heat damage indexes were calculated and analyzed. The representative symptoms of heat damage, including leaf crimple and warp, chlorosis of leaf, growth tardiness, wilting and death of the plants, were determined and scored. leaf crimple and warp: lightly, A; moderately, A+; seriously, A++;

chlorosis of leaf: lightly, B; moderately, B+; seriously, B++;

growth tardiness: lightly, C; moderately, C+; seriously, C++;

wilting and death: lightly, D; moderately, D+; seriously, D++.

The experimental results showed that the symptoms of heat damage in the transgenic plants of *Brassica campestris* L. ssp. *Pekinensis* plant were all scored as light, which was expressed as ABCD. The symptoms of heat damage in the control plants (wild type *Brassica campestris* L. ssp. *Pekinensis*, B-hot cabbage) were all scored as serious, which was expressed as A++B++C++D++.

The experimental results showed that the symptoms of heat damage in the transgenic plants of *Brassica campestris* L. ssp. *chinensis* plant were all scored as light, which was expressed as ABCD. The symptoms of heat damage in the control plants (wild type *Brassica campestris* L. ssp. *chinensis*, heat-sensitive *Brassica campestris* L. ssp. *chinensis* HS) were all scored as serious, which was expressed as A++B++C++D++.

It can be seen that, the transgenic plants of *Brassica campestris* L. ssp. *Pekinensis* and *Brassica campestris* L. ssp. *chinensis* are much more tolerant to the heat stress in bolting stage as compared to the wild type plants.

Example 5

Study on the Domains in the JAZ5a Protein, its Variants and Functions

The inventors of the subject application has identified the domains in the BccJAZ5a protein (SEQ ID NO:4), as shown in FIG. 5. The results showed that positions 101-130 constitute a tify domain, and the segment of 184-209 is a CCT_2 motif. These domains are the critical active site for the protein's heat-resistance function.

Based on the above analysis, the inventors constructed several variants of the BccJAZ5a protein as specified below:

In the sequence of the BccJAZ5a protein (SEQ ID NO:4), amino acid 9 was changed from A to V, so as to obtain BccJAZ5a-M1 variant.

In the sequence of the BccJAZ5a protein (SEQ ID NO:4), amino acid 253 was changed from L to I, so as to obtain BccJAZ5a-M2 variant.

In the sequence of the BccJAZ5a protein (SEQ ID NO:4), amino acid 147 was changed from V to A, so as to obtain BccJAZ5a-M3 variant, and amino acid 230 was changed from L to I. In the sequence of the BccJAZ5a protein (SEQ ID NO:4), amino acids 266-270 were deleted, so as to obtain BccJAZ5a-M4 variant.

In the sequence of the BccJAZ5a protein (SEQ ID NO:4), amino acids 159-161 were deleted, so as to obtain BccJAZ5a-M5 variant.

In the sequence of the BccJAZ5a protein (SEQ ID NO:4), four amino acids ATAA were added to the C-terminus, so as to obtain BccJAZ5a-M6 variant.

The CDS sequence of the BccJAZ5a gene shown in SEQ ID NO: 2 was first cloned into the pCAMBIA1300 vector at the Kpn I site to obtain a recombinant vector containing said CDS. Then, site-directed mutagenesis was conducted to introduce the corresponding substitution, deletion and addition to obtain the recombinant vectors containing the abovesaid variants respectively.

The recombinant vectors thus constructed were transformed into strains of *agrobacterium*, and then the *agrobacterium* strains were used to transform *Arabidopsis*, so that the following transgenic *Arabidopsis* plants were obtained: M1-Line1, M1-Line2; M2-Line1, M2-Line2; M3-Line1, M3-Line2; M4-Line1, M4-Line2; M5-Line1, M5-Line2; M6-Line1, M6-Line2.

A heat treatment system was used to verify the phenotype of these transgenic *Arabidopsis* plants. The plants grew at 22° C. until bolting. Then the plants were subjected to heat treatment at 45° C. for 3 hour, and then switched back to 22° C. for 5 days before photos were taken. For each lineage, two experiments in duplicate were conducted. The transgenic plants could better tolerate heat stress as compared the wild type plants.

In summary, BccJAZ5a of cabbage and its variants are effective heat-resistance gene which can be used to improve the heat resistance in plants in bolting stage.

All references cited in the present invention are incorporated herein by reference as each one of them was individually cited. Further, it is understood that various modifications and/or changes are obvious to a skilled person in the art, in view of the teaching of the current invention, falling within the scope as defined by the description and the claims.

The invention claimed is:

1. A method for providing a plant with improved heat resistance comprising introducing into the plant a heat-resistance protein comprising the amino acid sequence of SEQ ID NO:4 or having at least 95% sequence identity to the amino acid sequence of SEQ ID NO:4, or enhancing expression or activity of the heat-resistance protein in the plant.

2. The method of claim 1, wherein the heat-resistance protein comprises the amino acid sequence of SEQ ID NO:4.

3. The method of claim 1, wherein the heat-resistance protein consists of the amino acid sequence of SEQ ID NO:4.

4. The method according to claim 1, wherein the plant is a dicotyledon plant.

5. The method according to claim 1, wherein the plant is a monocotyledon plant.

6. The method according to claim 1, wherein the plant is selected from the group consisting of plants of Cruciferae, Gramineae and Rosaceae.

7. The method according to claim 1, wherein the plant is selected from the group consisting of wheat, barley, rye, rice, corn, sorghum, beet, apple, pear, plum, peach, apricot, cherry, strawberry, Rubus swinhoei Hance, blackberry, bean, lentil, pea, soy, rape, mustard, opium poppy, olea europea, helianthus, coconut, plant producing castor oil, cacao, peanut, calabash, cucumber, watermelon, cotton, flax, cannabis, jute, citrus, lemon, grapefruit, spinach, lettuce, asparagus, cabbage, *Brassica campestris L.* ssp. *Pekinensis, Brassica campestris L.* ssp. *chinensis*, carrot, onion, murphy, tomato, green pepper, avocado, cassia, camphor, tobacco, nut, coffee, aubergine, sugar cane, tea, pepper, grapevine, nettle grass, banana, natural rubber tree, and ornamental plant.

8. The method according to claim 1, wherein the step of providing or enhancing expression or activity of the heat-resistance protein in said plant comprises promoting the expression of the heat-resistance protein.

9. The method according to claim 1, wherein the step of providing or enhancing expression or activity of the heat-resistance protein in said plant comprises enhancing the activity of the heat-resistance protein.

10. The method according to claim 1, wherein the step of providing or enhancing expression or activity of the heat-resistance protein in said plant comprises enhancing the stability of the heat-resistance protein.

11. The method according to claim 1, wherein the step of providing or enhancing expression or activity of the heat-resistance protein in said plant comprises prolonging the effect duration of the heat-resistance protein.

12. The method according to claim 1, further comprises assessing heat resistance of a plant by detecting the presence of a molecular marker comprising at least 50 nucleotides of a polynucleotide sequence encoding the heat-resistance protein.

13. The method according to claim 12, wherein the polynucleotide sequence encoding the heat-resistance protein is SEQ ID NO:1 or SEQ ID NO:2.

14. The method according to claim 12, wherein the step of detecting the presence of the molecular marker comprises amplifying the at least 50 nucleotides of the polynucleotide sequence encoding the heat-resistance protein using a pair of primers represented by SEQ ID NO:5 and SEQ ID NO:6.

15. The method according to claim 12, further comprising molecular marker-assisted selection of a plant with improved heat resistance.

* * * * *

SEQUENCE LISTING

```
<160> NUMBER OF SEQ ID NOS: 18

<210> SEQ ID NO 1
<211> LENGTH: 1587
<212> TYPE: DNA
<213> ORGANISM: Brassica campestris L. ssp. chinensis

<400> SEQUENCE: 1
ataaaacaca tgagcgagct cgacgcatcc cacttctctt tcttccattt gacgcacaga     60
aaaaggaaaa ataagataac aaatacataa ctaaaaacaa acagaattct ggagaatctc    120
tccttattat tcacaatatg tcaagaaatg aagatggtga ggcaccaccg ccggagaagt    180
ccaacttcac ccggcgatgt agtttgctca gccgttactt gaaggagaag ggtagtttcg    240
gtaatataga tcttggattg gtccgaaagc ctggtccgga tctcgggtta cccggaaact    300
ctgatcaaca aggtacttta tatcttccta gctctcacgt ccgccacttg taatagtaaa    360
gtctggtttt attttattta tttgcaagtc acttccttaa aactcgaatt aatctacttt    420
tgtaatatgt aaccaggaaa atataagaag agaatttagt tgattttgga aactgatacg    480
gttcatgaat cgcaaaaaat aattattttt tgtagagttt attcgtttga tgattccaat    540
aaagcttata agagtttttt attctcttta ttcagagaaa caaaatgtga tgcataaggc    600
aaattcggaa ctcaaagccc ttaatgtctt aggcgaaccc tctagttcat ttggaggcaa    660
agccaaagct accaatctca ggtgagatct ataataatac ttgttgctct tccggtttta    720
aatggttctc ttctgaaacc ggattttggt ttacagtgaa ccatcagagc caattagttc    780
tcagctgaca atattctttg gaggaaaagt tctagtatac aatgagtttc cttcagacaa    840
agctaaagag ataatacagg tagcaaaaga agccaagtct gtgactgata ttaacattca    900
gacacaaatc aatgtccaaa aggaccacaa caaaagcaac atagttcttc ctgatctcaa    960
cgagcccaca gatactgcgg atgtcaatca acagcaacaa caacaaaacc agctcgtgga   1020
acgtatagca cgtagagctt ccttacatcg cttctttgct aaacgtaaag acaggtaaac   1080
atagcttgac tagttcaaaa gattatgtat ttgaaaacta taagtgctct taaatgatcc   1140
tagtaatcaa tcaaaaccgc gatagatact cacatgacaa ttttcgtata ttttgttttt   1200
tcatcacagg gctgtggcta gagctccata ccaagttaac caaaatggtg gtggtcatca   1260
ttatcctccg aagccagaga ctgtacctgg tcaacagcta gagcagggac agtcgtcaca   1320
accacaacga ccggctcaac ccaaaccaga atgtgataaa gatatgttga tggaagttaa   1380
```

```
ggaagaaggc cagtgttcga aagatctcga acttaggcta taatcaaatt ttgttaaata    1440
tttgtaagaa acttaaactt aagatgatcg tctgacttat tttaaatgat ttttgctttg    1500
tactaaagtt tgcaaccaat ttttaacttg gatattaata aatgcaatag tgaatttagt    1560
tgcaatttat aacaatttga tttgcaa                                         1587

<210> SEQ ID NO 2
<211> LENGTH: 813
<212> TYPE: DNA
<213> ORGANISM: Brassica campestris L. ssp. chinensis

<400> SEQUENCE: 2
atgtcaagaa atgaagatgg tgaggcacca ccgccggaga agtccaactt cacccggcga      60
tgtagtttgc tcagccgtta cttgaaggag aagggtagtt tcggtaatat agatcttgga    120
ttggtccgaa agcctggtcc ggatctcggg ttacccggaa actctgatca acaagagaaa    180
caaaatgtga tgcataaggc aaattcggaa ctcaaagccg ttaatgtctt aggcgaaccc    240
tctagttcat ttggaggcaa agccaaagct accaatctca gtgaaccatc agagccaatt    300
agttctcagc tgacaatatt cttggagga aagttctag tatacaatga gtttccttca    360
gacaaagcta aagagataat acaggtagca aaagaagcca agtctgtgac tgatattaac    420
attcagacac aaatcaatgt ccaaaaggac acaacaaaa gcaacatagt tcttcctgat    480
ctcaacgagc ccacagatac tgcggatgtc aatcaacagc aacaacaaca aaaccagctc    540
gtggaacgta tagcacgtag agcttcctta catcgcttct ttgctaaacg taaagacagg    600
gctgtggcta gagctccata ccaagttaac caaaatggtg gtggtcatca ttatcctccg    660
aagccagaga ctgtacctgg tcaacagcta gagcagggac agtcgtcaca accacaacga    720
ccggctcaac ccaaaccaga atgtgataaa gatatgttga tggaagttaa ggaagaaggc    780
cagtgttcga aagatctcga acttaggcta taa                                  813

<210> SEQ ID NO 3
<211> LENGTH: 1825
<212> TYPE: DNA
<213> ORGANISM: Brassica campestris L. ssp. chinensis

<400> SEQUENCE: 3
gaggcttaca ggttcaacca tttcagtaga accttccaac atctggaaac gatcaaagga     60
gcaactcttt gacagccgta cgatcaaaac tcatttgaca catctcagtt tctcactgac    120
ttcctctcag tcatcagctt tctccttctc tttcttcaga tctctgcttc ttctcctcgg    180
tttcaatgtc gctccatctt cttctccttc ttctgctact atcccttgga gcaccttctt    240
tgctccaagc gtcggtgcat gagtaccgta gcgagagatt catgtccaaa ggcaacgcct    300
ttgtcttcca cggcggcagt gaaggcatct actcctcttc tccctccgac aacttctcct    360
ccgactctga ttccctctcc tcctttatcc ggtaaagttc tatgattccg tttcttaac    420 taaagttcc tcttttaaat ctgcttagga tctgactttg taatcagaac ccattaggat    480
tcttcgtcta cgagttggat cttagagctg attaagttcg tttgtataca gttcttagct    540
gtttctcggt gaaagtttct tactttgaaa ctctgtgtgt gtcctctctg agtaagcatt    600
gcttccacgt gtcaaagatt tgaactttca ttgtgttttg agtaaaatct tagctgtttc    660
tctgtaaaag tttctaactt tgaaactctg tttgtatcct ctctgagtaa acatttcttc    720
cacgtgtcaa aagagctgaa ctttcctcgt gtttgagtaa catcttagct gtttctctgt    780
```

```
gaaagcttct tactttgaaa ctctgtgtgt gtcctctctg agtaaacatt gcttccacgt      840
gtcaaagagt tgaactttcc ttgtgtttga gtaacatctt agctgtttct ctgtgaaagt      900
ttcttacttg ctaatgcatt taacagtttt gagaagatca cattccggag acccgaggaa      960
gcttccaaca cctcttcatt acctatccac gccgtccttt tcgaggtaga agacagggag     1020
aacatcggag gatcagctta cggtgggcag agagctgtct gctgcacatc tgatctcgcc     1080
aaactcggtg tttgctcaca cggagagatc atccaccatc cttcttctaa agactcctcc     1140
tggcctcaag tcttcggtgt ttcctttgtt gagaatgatt tgtctgctac gctgcttaca     1200
agatcgattc agatcactag gacaggaatg tataacctct acttcatcca ctgtgatcct     1260
gctctcaagg acttggtcgt tgaaggcaaa accatctgga aaaaccctgg aggatactta     1320
ccaggtagaa tggctccgtt gatgtacttc tacgggttca tgtctctcgc ctttgtgctc     1380
ctcggagtct tctggttctc ccagtgcgct aggttctgga gagaagtgct tcccttgcag     1440
aactgtgtaa ctttagtgat aacgcttggg atgtgcgaga tggcgctttg gtacttcgac     1500
tacgctgagt tcaacgagac tggtgttaga ccaacggtga tcaccgtatg ggcagtcacg     1560
tttgggtgta tcaaacgcac gtgcgcacgt gtcatcatcc ttatggtttc gatggggtac     1620
ggtgtcgtga ggcctacgct tggtgggttt acatcgaagg tgatcatgct tggtgtcact     1680
ttcttcgctg cttccgagac tcttgagctg ttggagaatg ttggtgcggt tagtgacttc     1740
tcagggaaag cgagactgtt tttggttctc cccgttgcgg tgttggatgc tttcttcatc     1800
atatggatat tcaagtcgct ttcgg                                           1825

<210> SEQ ID NO 4
<211> LENGTH: 270
<212> TYPE: PRT
<213> ORGANISM: Brassica campestris L. ssp. chinensis

<400> SEQUENCE: 4

Met Ser Arg Asn Glu Asp Gly Glu Ala Pro Pro Glu Lys Ser Asn
1               5                   10                  15

Phe Thr Arg Arg Cys Ser Leu Leu Ser Arg Tyr Leu Lys Glu Lys Gly
            20                  25                  30

Ser Phe Gly Asn Ile Asp Leu Gly Leu Val Arg Lys Pro Gly Pro Asp
        35                  40                  45

Leu Gly Leu Pro Gly Asn Ser Asp Gln Gln Lys Gln Asn Val Met
    50                  55                  60

His Lys Ala Asn Ser Glu Leu Lys Ala Val Asn Val Leu Gly Glu Pro
65                  70                  75                  80

Ser Ser Ser Phe Gly Gly Lys Ala Lys Ala Thr Asn Leu Ser Glu Pro
                85                  90                  95

Ser Glu Pro Ile Ser Ser Gln Leu Thr Ile Phe Phe Gly Gly Lys Val
            100                 105                 110

Leu Val Tyr Asn Glu Phe Pro Ser Asp Lys Ala Lys Glu Ile Ile Gln
        115                 120                 125

Val Ala Lys Glu Ala Lys Ser Val Thr Asp Ile Asn Ile Gln Thr Gln
    130                 135                 140

Ile Asn Val Gln Lys Asp His Asn Lys Ser Ile Val Leu Pro Asp
145                 150                 155                 160

Leu Asn Glu Pro Thr Asp Thr Ala Asp Val Asn Gln Gln Gln Gln
                165                 170                 175

Gln Asn Gln Leu Val Glu Arg Ile Ala Arg Arg Ala Ser Leu His Arg
            180                 185                 190
```

Phe Phe Ala Lys Arg Lys Asp Arg Ala Val Ala Arg Ala Pro Tyr Gln
        195                 200                 205

Val Asn Gln Asn Gly Gly Gly His His Tyr Pro Pro Lys Pro Glu Thr
    210                 215                 220

Val Pro Gly Gln Gln Leu Glu Gln Gly Gln Ser Ser Gln Pro Gln Arg
225                 230                 235                 240

Pro Ala Gln Pro Lys Pro Glu Cys Asp Lys Asp Met Leu Met Glu Val
                245                 250                 255

Lys Glu Glu Gly Gln Cys Ser Lys Asp Leu Glu Leu Arg Leu
                260                 265                 270

```
<210> SEQ ID NO 5
<211> LENGTH: 18
<212> TYPE: DNA
<213> ORGANISM: Artificial Sequence
<220> FEATURE:
<223> OTHER INFORMATION: Primer

<400> SEQUENCE: 5
aagaagccaa gtctgtga                                                 18

<210> SEQ ID NO 6
<211> LENGTH: 18
<212> TYPE: DNA
<213> ORGANISM: Artificial Sequence
<220> FEATURE:
<223> OTHER INFORMATION: Primer

<400> SEQUENCE: 6
tcggaggata atgatgac                                                 18

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
gctaaacgga aagacagagc                                               20

<210> SEQ ID NO 8
<211> LENGTH: 19
<212> TYPE: DNA
<213> ORGANISM: Artificial Sequence
<220> FEATURE:
<223> OTHER INFORMATION: Primer

<400> SEQUENCE: 8
tgagggagac gaggacaag                                                19

<210> SEQ ID NO 9
<211> LENGTH: 19
<212> TYPE: DNA
<213> ORGANISM: Artificial Sequence
<220> FEATURE:
<223> OTHER INFORMATION: Primer

<400> SEQUENCE: 9
tctaatatgg tccgcaatc                                                19

<210> SEQ ID NO 10
<211> LENGTH: 18
```

```
<212> TYPE: DNA
<213> ORGANISM: Artificial Sequence
<220> FEATURE:
<223> OTHER INFORMATION: Primer

<400> SEQUENCE: 10
tttcaatccg tccaatct                                                     18

<210> SEQ ID NO 11
<211> LENGTH: 18
<212> TYPE: DNA
<213> ORGANISM: Artificial Sequence
<220> FEATURE:
<223> OTHER INFORMATION: Primer

<400> SEQUENCE: 11
aaaatgctaa ggcacaag                                                     18

<210> SEQ ID NO 12
<211> LENGTH: 18
<212> TYPE: DNA
<213> ORGANISM: Artificial Sequence
<220> FEATURE:
<223> OTHER INFORMATION: Primer

<400> SEQUENCE: 12
gatgaggtag agggttcg                                                     18

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
tccgtccacc ttgtagaact g                                                 21

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
tgaaaaccct aacggggaaa                                                   20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
tggcatcaya ctttctacaa                                                   20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
```

```
ccaccactda gcacaatgtt                                              20

<210> SEQ ID NO 17
<211> LENGTH: 18
<212> TYPE: DNA
<213> ORGANISM: Artificial Sequence
<220> FEATURE:
<223> OTHER INFORMATION: Primer

<400> SEQUENCE: 17
ctttcttcca tttgacgc                                                18

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18
ctgcaactaa attcactatt g                                            21
```